(12) United States Patent
Shipley et al.

(10) Patent No.: US 7,855,182 B2
(45) Date of Patent: Dec. 21, 2010

(54) MATERIALS AND METHODS FOR TREATMENT OF CANCER

(75) Inventors: Janet Shipley, Sutton (GB); Daniel Williamson, London (GB); Jane Renshaw, Sutton (GB); Rosanne Orr, Sutton (GB)

(73) Assignee: The Institute of Cancer Research; Royal Cancer Hospital, London (GB)

( * ) Notice: Subject to any disclaimer, the term of this patent is extended or adjusted under 35 U.S.C. 154(b) by 310 days.

(21) Appl. No.: 10/593,597

(22) PCT Filed: Mar. 22, 2005

(86) PCT No.: PCT/GB2005/001085

§ 371 (c)(1),
(2), (4) Date: Jun. 12, 2008

(87) PCT Pub. No.: WO2005/092379

PCT Pub. Date: Oct. 6, 2005

(65) Prior Publication Data

US 2008/0241825 A1    Oct. 2, 2008

(30) Foreign Application Priority Data

Mar. 22, 2004  (GB) ................................ 0406415.0

(51) Int. Cl.
*A61K 48/00*    (2006.01)

(52) U.S. Cl. ........................................................ 514/44
(58) Field of Classification Search .................... 514/44
See application file for complete search history.

(56) References Cited

FOREIGN PATENT DOCUMENTS

WO    WO 03/006611 A2    1/2003

OTHER PUBLICATIONS

Fitzgibbon, et al., "Refinement and evaluation of candidate genes within the 13q amplicon in germinal centre lymphoma", Bllod, vol. 100, No. 11, p. ABS. No. 4258, (2002).
Ota, et al., "Identification and characterization of a novel gene, C13orf25, as a target for 13q31-q32 amplification in malignant lymphoma", Cancer Research, vol. 64, No. 9, pp. 3087-3095, (2004).
Yu, et al., "GPC5 is a possible target for the 13q31-q31 amplification detected in lymphoma cell lines", Journal of Human Genetics, vol. 48, pp. 331-335, (2003).
Dean et al., "*Antisense oligonucleotide-based therapeutics for cancer*", Oncogene (2003) 22, p. 9087-9096.

*Primary Examiner*—J. E Angell
(74) *Attorney, Agent, or Firm*—Arnold & Porter LLP; Ginger R. Dreger

(57) ABSTRACT

Glypican 5 is shown for the first time to have a role in proliferation of cancer cells, including tumors which do not show chromosomal amplification at 13q31. The use of glypican 5 (GPC5) antagonists and binding agents for the treatment of cancer, particularly rhabdomyosarcoma and breast cancer, is disclosed.

10 Claims, 11 Drawing Sheets

(A)

Log GPC5 expression relative to normal muscle

Log GPC5 expression relative to normal muscle (B)

(B)
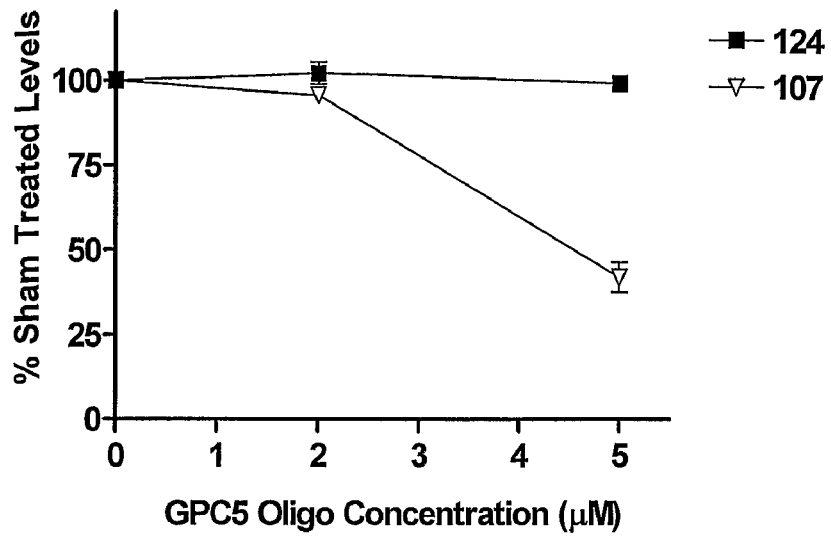
(C)
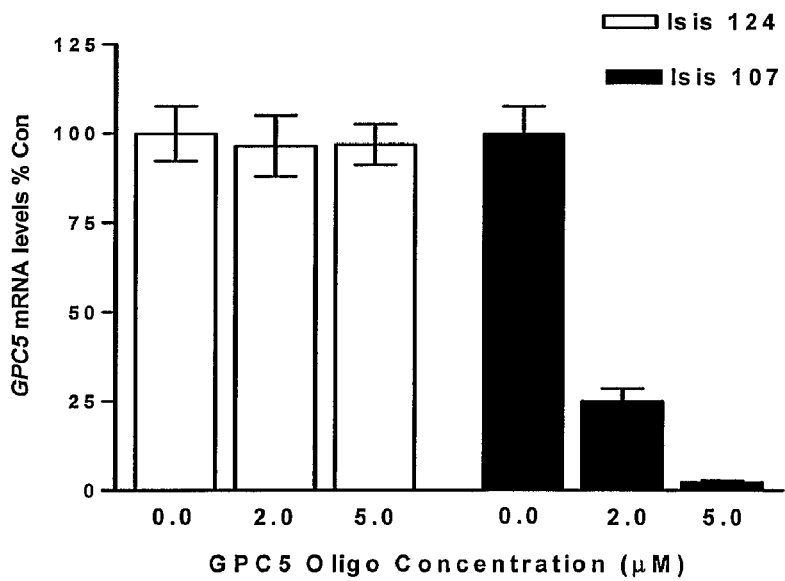
Figure 3 (contd.)

(A)

(B)

(A)

(B)

SEQUENCE LISTING

```
<160> NUMBER OF SEQ ID NOS: 28

<210> SEQ ID NO 1
<211> LENGTH: 16
<212> TYPE: PRT
<213> ORGANISM: Artificial Sequence
<220> FEATURE:
<223> OTHER INFORMATION: Epitope peptide

<400> SEQUENCE: 1

Cys Lys Ser Tyr Thr Gln Arg Val Val Gly Asn Gly Ile Lys Ala Gln
 1               5                  10                  15

<210> SEQ ID NO 2
<211> LENGTH: 30
<212> TYPE: DNA
<213> ORGANISM: Artificial Sequence
<220> FEATURE:
<223> OTHER INFORMATION: Forward primer for the quantification of WT1

<400> SEQUENCE: 2
tacccaggct gcaataagag atattttaag                                    30

<210> SEQ ID NO 3
<211> LENGTH: 24
<212> TYPE: DNA
<213> ORGANISM: Artificial Sequence
<220> FEATURE:
<223> OTHER INFORMATION: Reverse primer for the quantification of WT1

<400> SEQUENCE: 3
cctttggtgt cttttgagct ggtc                                          24

<210> SEQ ID NO 4
<211> LENGTH: 38
<212> TYPE: DNA
<213> ORGANISM: Artificial Sequence
<220> FEATURE:
<223> OTHER INFORMATION: Probe for the quantification of WT1

<400> SEQUENCE: 4
cactggtgag aaaccatacc agtgtgactt caaggact                           38

<210> SEQ ID NO 5
<211> LENGTH: 24
<212> TYPE: DNA
<213> ORGANISM: Artificial Sequence
<220> FEATURE:
<223> OTHER INFORMATION: GPC5 Forward primer

<400> SEQUENCE: 5
cccacccaaa tctcatctag aatt                                          24
```

```
<210> SEQ ID NO 6
<211> LENGTH: 23
<212> TYPE: DNA
<213> ORGANISM: Artificial Sequence
<220> FEATURE:
<223> OTHER INFORMATION: GPC5 Probe - FAM labelled

<400> SEQUENCE: 6
ccgggttcct ccctttgcac atg                                              23

<210> SEQ ID NO 7
<211> LENGTH: 21
<212> TYPE: DNA
<213> ORGANISM: Artificial Sequence
<220> FEATURE:
<223> OTHER INFORMATION: GPC5 Reverse primer

<400> SEQUENCE: 7
acgcattgcc cagttgttag a                                                21

<210> SEQ ID NO 8
<211> LENGTH: 25
<212> TYPE: DNA
<213> ORGANISM: Artificial Sequence
<220> FEATURE:
<223> OTHER INFORMATION: GJB2 Forward primer

<400> SEQUENCE: 8
tggttgcatt taaggtcaga atctt                                            25

<210> SEQ ID NO 9
<211> LENGTH: 27
<212> TYPE: DNA
<213> ORGANISM: Artificial Sequence
<220> FEATURE:
<223> OTHER INFORMATION: GJB2 Probe - Vic Labelled

<400> SEQUENCE: 9
ctagcgactg agccttgaca gctgagc                                          27

<210> SEQ ID NO 10
<211> LENGTH: 19
<212> TYPE: DNA
<213> ORGANISM: Artificial Sequence
<220> FEATURE:
<223> OTHER INFORMATION: GJB2 Reverse primer

<400> SEQUENCE: 10
gcagaggcac gttcaggaa                                                   19

<210> SEQ ID NO 11
<211> LENGTH: 15
<212> TYPE: DNA
<213> ORGANISM: Artificial Sequence
<220> FEATURE:
<223> OTHER INFORMATION: GPC5 Forward primer

<400> SEQUENCE: 11
gggctgccgg attcg                                                       15

<210> SEQ ID NO 12
<211> LENGTH: 22
<212> TYPE: DNA
<213> ORGANISM: Artificial Sequence
<220> FEATURE:
<223> OTHER INFORMATION: GPC5 Probe - FAM labelled
```

```
<400> SEQUENCE: 12
cgcgggcagg acctgatctt ca                                          22

<210> SEQ ID NO 13
<211> LENGTH: 22
<212> TYPE: DNA
<213> ORGANISM: Artificial Sequence
<220> FEATURE:
<223> OTHER INFORMATION: GPC5 Reverse primer

<400> SEQUENCE: 13
ctggtgcaac atgtaggctt tt                                          22

<210> SEQ ID NO 14
<211> LENGTH: 20
<212> TYPE: DNA
<213> ORGANISM: Artificial Sequence
<220> FEATURE:
<223> OTHER INFORMATION: GPC6 Forward primer

<400> SEQUENCE: 14
tgaccagctc aagccatttg                                             20

<210> SEQ ID NO 15
<211> LENGTH: 26
<212> TYPE: DNA
<213> ORGANISM: Artificial Sequence
<220> FEATURE:
<223> OTHER INFORMATION: GPC6 Probe - FAM labelled

<400> SEQUENCE: 15
agacgtgccc cggaaactga agattc                                      26

<210> SEQ ID NO 16
<211> LENGTH: 17
<212> TYPE: DNA
<213> ORGANISM: Artificial Sequence
<220> FEATURE:
<223> OTHER INFORMATION: GPC6 Reverse primer

<400> SEQUENCE: 16
tgaaggcgcg ggtaacc                                                17

<210> SEQ ID NO 17
<211> LENGTH: 20
<212> TYPE: DNA
<213> ORGANISM: Artificial Sequence
<220> FEATURE:
<223> OTHER INFORMATION: GPC6 Forward primer

<400> SEQUENCE: 17
aacgaggagg aatgctggaa                                             20

<210> SEQ ID NO 18
<211> LENGTH: 30
<212> TYPE: DNA
<213> ORGANISM: Artificial Sequence
<220> FEATURE:
<223> OTHER INFORMATION: GPC6 Probe - FAM labelled

<400> SEQUENCE: 18
cacagcaaag ccagatactt gcctgagatc                                  30

<210> SEQ ID NO 19
```

```
<211> LENGTH: 20
<212> TYPE: DNA
<213> ORGANISM: Artificial Sequence
<220> FEATURE:
<223> OTHER INFORMATION: GPC6 Reverse primer

<400> SEQUENCE: 19
ctggttggtg agcccatcat                                                    20

<210> SEQ ID NO 20
<211> LENGTH: 36
<212> TYPE: DNA
<213> ORGANISM: Artificial Sequence
<220> FEATURE:
<223> OTHER INFORMATION: GPC5 Forward primer

<400> SEQUENCE: 20
tataagcttc caccatggac gcacagacct ggcccg                                  36

<210> SEQ ID NO 21
<211> LENGTH: 29
<212> TYPE: DNA
<213> ORGANISM: Artificial Sequence
<220> FEATURE:
<223> OTHER INFORMATION: GPC5 Reverse primer

<400> SEQUENCE: 21
cgcgtcgact taccaaatcc cgggaagta                                          29

<210> SEQ ID NO 22
<211> LENGTH: 20
<212> TYPE: DNA
<213> ORGANISM: Artificial Sequence
<220> FEATURE:
<223> OTHER INFORMATION: ISIS 15770, a 5-10-5 gapmer targeting murine
      c-raf kinase used as a control

<400> SEQUENCE: 22
atgcattctg cccccaagga                                                    20

<210> SEQ ID NO 23
<211> LENGTH: 20
<212> TYPE: DNA
<213> ORGANISM: Artificial Sequence
<220> FEATURE:
<223> OTHER INFORMATION: ISIS 276107, an antisense oligonucleotide

<400> SEQUENCE: 23
cagccccctg acagctccca                                                    20

<210> SEQ ID NO 24
<211> LENGTH: 20
<212> TYPE: DNA
<213> ORGANISM: Artificial Sequence
<220> FEATURE:
<223> OTHER INFORMATION: ISIS 276119, an antisense oligonucleotide

<400> SEQUENCE: 24
ccatctgcag cagctaattc                                                    20

<210> SEQ ID NO 25
<211> LENGTH: 20
<212> TYPE: DNA
<213> ORGANISM: Artificial Sequence
<220> FEATURE:
<223> OTHER INFORMATION: ISIS 276124, a control antisense
      oligonucleotide
```

```
<400> SEQUENCE: 25
tggatttgct ttacatcact                                              20

<210> SEQ ID NO 26
<211> LENGTH: 20
<212> TYPE: DNA
<213> ORGANISM: Artificial Sequence
<220> FEATURE:
<223> OTHER INFORMATION: ISIS 16609, a previously identified antisense
      oligonucleotide targeting WT1 exon 5

<400> SEQUENCE: 26
gcccttctgt ccatttcact                                              20

<210> SEQ ID NO 27
<211> LENGTH: 20
<212> TYPE: DNA
<213> ORGANISM: Artificial Sequence
<220> FEATURE:
<223> OTHER INFORMATION: ISIS 16601, a previously identified antisense
      oligonucleotide targeting the 3prime-UTR region of WT1

<400> SEQUENCE: 27
cacatacaca tgccctggcc                                              20

<210> SEQ ID NO 28
<211> LENGTH: 20
<212> TYPE: DNA
<213> ORGANISM: Artificial Sequence
<220> FEATURE:
<223> OTHER INFORMATION: ISIS 105730, a control antisense
      oligonucleotide

<400> SEQUENCE: 28
ccatcgacct gcaccgatca                                              20
```

MATERIALS AND METHODS FOR TREATMENT OF CANCER

RELATED APPLICATIONS

This application is a National Stage filed under 35 USC §371 of PCT Application No. PCT/GB2005/001085 filed Mar. 22, 2005, which claims the benefit of United Kingdom Application No. 0406415.0 filed Mar. 22, 2004, the entire disclosures of which are hereby expressly incorporated by reference.

FIELD OF THE INVENTION

The present invention relates to the treatment of cancer, and in particular to the use of glypican 5 (GPC5) antagonists and binding agents for the treatment of cancers.

BACKGROUND OF THE INVENTION

Amplification of genomic regions is frequently observed in human tumors and is one mechanism leading to the upregulation of genes that may critically affect cellular behaviour and drive tumour progression. Therefore, identifying the genes involved in amplification events represents a useful approach to increasing understanding of tumorigenic processes and may provide clinically useful markers.

Rhabdomyosarcomas (RMS) are the most common soft tissue sarcomas of childhood and account for around 5% of all childhood cancers. There are two main histological subtypes of RMS namely, alveolar (ARMS) and embryonal (ERMS). Both subtypes consist of cells that resemble and have markers for developing skeletal muscle. The alveolar subtype is generally associated with a poorer prognosis than ERMS and often has a t(2;13) (q35;q14) or t(1;13) (p36;q14) translocation which fuses the PAX3 or PAX7 genes, respectively, to FOXO1A (1-3). In addition to these translocations a number of other aberrations have been defined including regions of genomic amplification (4-10). There are a small but significant group of ERMS which demonstrate a poor response to treatment; the genetics of this group is not well defined.

Our previous work on RMS showed amplification of the 13q31-q32 chromosomal region in around 20% of ARMS studied (4). In addition, samples from a number of other tumour types have been reported with amplification of the 13q31-32 region including other sarcomas (leiomyosarcomas (11), malignant fibrous histiocytomas (12), lymphomas (13), breast cancers (14), small cell lung carcinomas and various neurological tumours (15-17)). Also, the widely available leukaemic cell line K562 has been shown to have amplification of the 13q31-32 region in addition to the translocation associated with the BCR-ABL fusion gene (18). Recent work on a few lymphoma cell lines derived from different types of lymphoma defined a minimum region of amplification at 13q31-32 to an approximately 4 megabase region (13). This region contained the glypican 5 gene (GPC5) which was shown to be expressed and was suggested as a possible target for the amplification event in lymphomas. Whether this gene plays a functional role in lymphomas and whether the same gene is involved in other tumour types with genomic aberrations in this region remains to be determined.

In a previous analysis of RMS samples we used a new approach to profile global changes in differential expression which targets chromosomes called comparative expressed sequence hybridization (CESH) (19). The data from 45 cases was used in a study to examine the classification potential of these profiles (20). Here we compare chromosomal level genetic and expression data for the 13q31-32 region and suggest that amplification is not the only mechanism leading to increased expression of gene(s) from this region. In view of the frequent differential expression from the 13q31-32 region in addition to its amplification we have sought to implicate gene(s) from this region in the development of RMS. This could provide a target for therapeutic approaches to treat these, and potentially other tumours.

SUMMARY OF THE INVENTION

As described above, amplification of 13q31 has been observed in alveolar RMS and a number of other cancer types. Yu et al. (13) have further shown that the GPC5 gene is overexpressed in lymphoma cell lines having an amplicon at 13q31-32, as compared to cell lines lacking that amplicon. While those authors speculated that GPC5 might play a role in the pathogenesis of lymphomas with amplification of 13q31-32, they did not provide any evidence of this. Tumour cells are notoriously genetically unstable, being prone to acquiring genetic abnormalities, such as chromosomal amplifications, after transformation. It is therefore possible that the observed amplification was acquired after transformation, or alternatively is simply not involved in the transformation process. Accordingly, there is no proof in the literature to date that GPC5 has any role in normal or abnormal cell proliferation.

The present inventors have demonstrated that downregulation of GPC5 expression in cells which overexpress it reduces the ability of these cells to form colonies in vitro. The inventors have therefore shown for the first time that GPC5 expression is directly linked to cellular proliferation, thus providing a novel therapeutic target.

Furthermore, the inventors have found that GPC5 is overexpressed in tumours which do not show chromosomal amplification at 13q31.

The inventors have also found evidence to suggest that GPC5 may be regulated by the Wilms' Tumour (WT1) gene product. WT1 is a zinc finger transcription factor which has been shown to be inappropriately and/or over expressed in leukaemias and a wide range of solid tumours including prostate, breast and lung, as well as thyroid, testicular and ovarian carcinomas, melanoma and mesothelioma (reviewed in Reddy, J. C., and Licht, J. D. (1996) Biochim Biophys Acta 1287, 1-28; Scharnhorst, V., van der Eb, A. J., and Jochemsen, A. G. (2001) Gene 273, 141-161). The fact that GPC5 is associated with MYCN and WT1 which are genes of known significance in tumours is consistent with GPC5 itself being of importance in tumorigenesis.

In tumour cells grown either in vitro or in vivo, downregulation of WT1 results in the concomitant downregulation of GPC5. Conversely, upregulation of WT1 results in the upregulation of GPC5. Direct transcriptional regulation of GPC5 by WT1 is likely since GPC5 has two WT1 consensus binding sites in its promoter region. Overexpression of WT1 may therefore drive the overexpression of GPC5 in tumours which do not carry chromosomal 13q31-32 amplicons and GPC5 expression may be modulated indirectly by targeting the expression of WT1. Downregulation of WT1 using antisense oligonucleotides results in inhibition of cell proliferation and induction of apoptosis (Algar, E. M., Khromykh, T., Smith, S. I., Blackburn, D. M., Bryson, G. J., and Smith, P. J. (1996) Oncogene 12, 1005-1014). Inhibition of proliferation may be wholly or partially mediated by downregulated GPC5 in some cell types.

Expression of high levels of WT1 is associated with poor prognosis in leukaemias and breast cancer. Evidence in the literature suggests that WT1 may contribute to drug resistance mechanisms through interference with cell checkpoint control and apoptotic pathways. However definitive evidence is lacking. The inventors have demonstrated upregulation of WT1 in chemoresistant tumour cell lines treated with cytotoxic drugs, a phenomenon absent in sensitive cell lines. Associated upregulation of GPC5 has also been demonstrated. Upregulation of GPC5 may mediate some of the effects of upregulated WT1 and contribute to chemoresistance mechanisms. Similarly, overexpression of GPC3 has recently been implicated in resistance to mitoxantrone and etoposide in a cell line model (Wichert et al. Oncogene 23: 945-955 2004). Inhibition of GPC5 activity either by direct or indirect downregulation of expression, or by blocking its activity, may increase the potency of some classes of cytotoxic drugs, particularly in cancers which inappropriately express or overexpress WT1.

The inventors' work therefore suggests a number of ways in which GPC5 may be targeted therapeutically. GPC5 is a cell surface molecule; agents capable of binding to GPC5 may therefore be used to direct therapeutic agents to target cells. Additionally or alternatively, antagonists which inhibit the expression or function of GPC5 at the cell surface can be used to inhibit cell proliferation directly. Furthermore, such GPC5 antagonists may also be used to increase the sensitivity of target cells to other chemotherapeutic agents, and so may be of significance in treating tumours that have become resistant to therapy.

Thus the therapeutic application of the inventors' findings extends far beyond those few cancers carrying chromosomal 13q31 amplicons.

Thus, in a first aspect, the present invention provides a method of inhibiting proliferation of a target cell, comprising contacting the cell with a GPC5 antagonist or a GPC5 binding agent.

In this aspect of the invention, a GPC5 binding agent is typically an agent capable of binding to GPC5 protein, that is to say to the GPC5 core protein and/or its associated heparan sulphate chains. Preferred GPC5 binding agents are antibodies, although peptides and small molecule binding agents may also be suitable.

The GPC5 binding agent may be used to direct a therapeutic agent capable of inhibiting proliferation of the target cell to the appropriate cell type. Thus the method may comprise the step of contacting the cell with a therapeutic agent.

The therapeutic agent may be part of, or associated with (covalently or non-covalently bonded or otherwise linked to), the binding agent. Alternatively the binding agent may be used to label a target cell in order that a suitable therapeutic agent can then be directed to the cell in preference to unlabelled cells, or activated in the vicinity of the cell. In such embodiments the therapeutic agent may be capable of binding to the GPC5 binding agent.

The skilled person will be aware of numerous possible mechanisms by which suitable therapeutic agents can be directed to a target cell via a GPC5 binding agent.

The therapeutic agent may comprise a cell or molecule of the immune system. For example, an anti-GPC5 antibody bound to a target cell may be capable of recruiting various effector mechanisms of the immune system to attack that cell. These include cellular mechanisms, such as antibody-directed cell-mediated cytotoxicity, which is mediated by polymorphonuclear cells, mononuclear cells and K cells, as well as molecular mechanisms such as the complement cascade.

Alternatively, the therapeutic agent may comprise a molecule capable of directly killing or inhibiting proliferation of the cell, such as a toxin or drug. This approach includes the use of precursor molecules capable of being converted to toxin or drug molecules by action of an enzyme expressed by the cell or associated with the GPC5 binding agent. An example of such a method is often referred to as ADEPT therapy (see below).

In yet further alternative embodiments the therapeutic agent may comprise a vector, such as a viral vector, comprising nucleic acid encoding a toxic or inhibitory agent to be synthesised within the cell. In such cases the agent encoded by the vector may itself be a GPC5 antagonist as described elsewhere in this specification.

These approaches may be used individually or in combination. Other suitable embodiments will be apparent to the skilled person.

A GPC5 binding agent may (but need not) have GPC5 antagonist activity in its own right.

A GPC5 antagonist is an agent which inhibits either the activity of GPC5 or the expression of functional GPC5 on the cell surface. Thus a GPC5 antagonist may inhibit cellular proliferation by directly blocking the proliferative effects of GPC5.

GPC5 antagonists which affect GPC5 activity (rather than expression) are typically GPC5 binding agents which prevent or inhibit the GPC5 protein from exerting its physiological activity, e.g. by blocking GPC5 from binding to a ligand, receptor, and/or co-receptor. For example, an antibody, peptide, small molecule or the like which performs any one of these functions may be regarded as a GPC5 antagonist as well as a GPC5 binding agent.

GPC5 antagonists which inhibit GPC5 expression may act at any one of a number of points in the generation of mature GPC5 protein. For example, the antagonist may inhibit transcription of the GPC5 gene, processing of GPC5 pre-mRNA, translation of GPC5 mRNA into protein, glycosylation of GPC5 (i.e. addition of carbohydrate residues to the GPC5 core protein) or processing of the carbohydrate chains into mature heparan sulphate (HS) chains.

Preferred antagonists of GPC5 expression comprise nucleic acid sequences complementary to the sequence of GPC5 mRNA or pre-mRNA. These include antisense RNA, dsRNA molecules (including RNAi and siRNA), and ribozymes.

As set out above, GPC5 antagonists may sensitize target cells to cytotoxic agents. Thus the method may comprise the further step of contacting the cell with a cytotoxic agent, wherein the GPC5 antagonist increases the sensitivity of the cell to the cytotoxic agent. This may be particularly useful in treatment of cancer patients whose cells have become resistant to a chemotherapeutic agent; the GPC5 antagonist may be used in combination with the chemotherapy to increase the efficacy of the chemotherapeutic agent.

Methods of the invention have applications both in vitro and in vivo, but as will be clear from the above, preferred aspects involve the administration of GPC5 antagonists or binding agents to subjects suffering from cancer, in order to inhibit proliferation of cancer cells.

Thus the invention further provides a method of treating cancer, comprising administering a GPC5 antagonist or a GPC5 binding agent to a subject suffering therefrom.

The invention further provides a GPC5 antagonist or a GPC5 binding agent as described herein for use in a method of medical treatment.

Also provided is use of a GPC5 antagonist or a GPC5 binding agent as described herein in the preparation of a medicament for the treatment of cancer.

In all of the therapeutic methods and compositions described herein, the GPC5 antagonists and binding agents may be used alone or in combination with other therapeutic agents, including cytotoxic agents (see above).

In a further aspect, the invention provides a method of determining the susceptibility of a cancer to treatment with a GPC5 antagonist or binding agent, comprising determining the presence, absence or level of expression of GPC5 in a cell from said cancer. Additionally or alternatively, the method may comprise the step of determining the presence, absence or degree of chromosomal amplification at 13q31, e.g. determining the genomic copy number of the GPC5 gene. Additionally or alternatively the method may comprise the step of determining the presence, absence or degree of WT1 expression in the cell. The cell may previously have been found to express WT1 inappropriately or to overexpress WT1. Determinations may be qualitative, quantitative or semi-quantitative.

The method will typically be performed in vitro using a sample isolated from a subject suffering from the cancer in question. The sample may comprise whole cells or cell extracts and may be derived from a biopsy, a body fluid such as blood, or any other suitable sample suspected or known to contain one or more cancer cells. The method may comprise the step of isolating the sample from the subject.

Typically the method will comprise the step of contacting the sample with a GPC5 binding agent, which in this aspect of the invention may be capable of binding to GPC5 protein, DNA or RNA. The method may further comprise the step of determining the amount of binding agent bound to GPC5 and correlating the results obtained with a likelihood that the cancer will be susceptible to treatment with a GPC5 antagonist or binding agent.

The presence or level of free circulating GPC5 (i.e. GPC5 protein not bound to a cell surface via a GPI anchor) may also serve as a marker for a cancer in which GPC5 is overexpressed. Thus in a further aspect the invention provides a method of screening for the presence of a cancer in a patient, the method comprising contacting a sample derived from the patient with a GPC5 binding agent. Preferably the sample is a sample of a body fluid, such as whole blood, serum, plasma urine, etc.

The method may further comprise the step of determining the amount of binding agent bound to GPC5 and correlating the results obtained with a likelihood that the patient has cancer.

The inventors have also found that overexpression of GPC5 in breast cancer samples correlates well with the stage of that cancer. In particular, tumours which overexpress GPC5 are significantly more likely to be stage 3 tumours than stage 1 or stage 2 tumours. This implies that GPC5 can be used as a prognostic marker for breast cancer.

Therefore the invention provides a method for determining a prognosis for a patient with breast cancer comprising assigning a prognosis to the patient based on the expression levels of GPC5 in a breast tumour from that patient.

The method typically comprises determining the presence, absence or degree of expression of GPC5 in a sample containing breast cancer cells. The method is typically performed in vitro using a sample isolated from the patient, although in vivo methods may also be envisaged. The sample may be contacted with a GPC5 binding agent capable of binding to GPC5 mRNA or protein.

"Prognosis" is intended in its most general sense, and may be quantitative or qualitative. It may be expressed in general terms, such as a "good" or "bad" prognosis, and/or in terms of likely clinical outcomes, such as duration of disease free survival (DFS), likelihood of survival for a defined period of time, and/or probability of distant metastasis within a defined period of time. Quantitative measures of prognosis will generally be probabilistic. Additionally or alternatively, and especially for communicating the prognosis to or between medical practitioners, the prognosis may be expressed in terms of another indicator of prognosis, such as the NPI scale.

In general, a patient with a 'good prognosis' tumour would probably be treated with a conventional treatment regimen. A patient with a 'poor prognosis' tumour might be treated with an alternative or more aggressive regimen. The 'poor prognosis' patient would usually not have to wait for the conventional treatment regimen to fail before moving onto the more aggressive one. Furthermore, having an understanding of the likely clinical course of the disease allows a patient to prepare a realistic plan for future, which is an important social aspect of cancer treatment.

For the avoidance of doubt, the term "determining" need not imply absolute certainty in prognosis. Rather, the expression levels of GPC5 in a tumour will generally be indicative of the likely prognosis of the patient.

Those patients whose tumours are found to overexpress GPC5 are likely to have stage 3 tumours, which may result in them being assigned a poor prognosis. It will be understood, though that GPC5 will not necessarily be the sole marker used in determination of prognosis. Rather, it may be used in combination with other prognostic makers to assist in reaching a detailed prognosis.

The inventors envisage that GPC5 expression may also be used to monitor the progress (e.g. success or failure) of a treatment for a cancer previously found to express GPC5. Such methods typically involve monitoring GPC5 expression in cells of the cancer. This may involve determining the level of expression of GPC5 within cells of the cancer. A reduction in the level of GPC5 expression over time may be taken as an indication that the treatment is effective. Additionally or alternatively, the method may involve determining the number or density of cells in a given sample expressing or overexpressing GPC5. This may assist in determining whether the size of the tumour is being reduced, so giving an indication of whether the treatment is having the desired effect of reducing tumour size.

The method will typically involve comparing the results obtained with results of an equivalent assay performed for the same patient before treatment, and/or at an earlier stage of treatment.

The method typically comprises determining the presence, absence or degree of expression of GPC5, or the number or density of cells expressing or overexpressing GPC5, in a sample containing breast cancer cells from the patient. As with other methods described herein, it is typically performed in vitro using a sample isolated from the patient, although in vivo methods may also be envisaged. The sample is typically contacted with a GPC5 binding agent capable of binding to GPC5 mRNA or protein.

In a further aspect the invention further provides methods of screening which may be used to identify therapeutic agents. In particular the invention provides a method of screening for an agent capable of killing or inhibiting proliferation of a target cell, comprising the steps of:

(i) contacting GPC5 protein with one or more candidate substances;

(ii) selecting one or more candidate substances based on their ability to bind GPC5 protein;

(iii) contacting said one or more selected substances with a target cell; and (iv) determining the effect of said selected substance(s) on proliferation of said cell.

The cell typically expresses GPC5, and preferably inappropriately expresses or overexpresses GPC5. The cell may naturally express GPC5 (e.g. it may be derived from a cancer in which GPC5 is expressed or overexpressed) or it may have been engineered to express GPC5, e.g. by transformation with a vector comprising nucleic acid encoding GPC5. The cell may previously have been found to inappropriately express or overexpress WT1.

The method may comprise the step of further selecting one or more substances found to inhibit proliferation of the target cell. The selected substances may be subjected to one or more rounds of modification, to increase activity and/or suitability for in vivo administration and re-tested for the ability to inhibit cellular proliferation. Suitable substances may be formulated for therapeutic administration, e.g. as a pharmaceutical composition.

In the various methods described above, the target cell or cancer cell typically overexpresses GPC5 mRNA and/or GPC5 protein. The cell may also carry a chromosomal amplicon comprising part or all of the 13q31 region; i.e. the cell may carry more than the normal two genomic copies of the GPC5 gene. In preferred embodiments, though, the cell overexpresses GPC5 but does not carry any amplification of that chromosomal region. The target cell is typically a cancer cell, and preferably one which overexpresses GPC5.

Cancers previously found to carry 13q31-32 amplicons include examples of rhabdomyosarcomas, including both embryonal and alveolar RMS, lymphomas including follicular lymphoma, mantle cell lymphoma and primary cutaneous B-cell lymphoma, non-small cell lung cancer, bladder cancer, a small proportion of breast cancers, neuroglial tumours including malignant peripheral nerve sheath tumours, squamous cell carcinoma of the head and neck, chronic myeloid leukemia, leiomyosarcoma, liposarcoma, malignant fibrous histocytoma of bone and soft tissues, (See Gordon et al., 2000, Yu et al., 2003, and references cited therein).

In view of the finding that GPC5 overexpression occurs in the absence of chromosomal amplification in RMS, prostate cancer and breast cancer, it is likely that examples of the above described cancer types will also overexpress GPC5 without 13q31 amplification and so any of the above are envisaged as suitable for treatment by the methods and compositions described in this specification.

GPC5 expression appears to be regulated (at least in part) by WT1. Accordingly, cancers which show inappropriate expression (e.g. overexpression) of WT1 may also be suitable for treatment by the methods described. These include leukaemias and a wide range of solid tumours including prostate, breast and lung, as well as thyroid, testicular and ovarian carcinomas, melanoma and mesothelioma (Scharnhorst, V., van der Eb, A. J., and Jochemsen, A. G. (2001) Gene 273, 141-161).

WT1 expression has also been implicated in the resistance of cancer cells to chemotherapeutic agents. Thus, cancers which are resistant to treatment with one or more cytotoxic agents may also be suitable for treatment according to the present invention. The cells may have been resistant ab initio or may have developed a resistance over the course of treatment. Typically such cells will be characterized by overexpression of WT1 and GPC5.

In addition, improved efficacy of GPC5 antagonists in increasing chemosensitivity may be achieved by concomitant down regulation of WT1 using WT1 antagonists. Preferred WT1 antagonists comprise nucleic acid sequences complementary to the sequence of WT1 mRNA or pre-mRNA. These include antisense RNA, dsRNA molecules (including RNAi and siRNA), and ribozymes.

DETAILED DESCRIPTION OF THE INVENTION

Glypicans

Figure 1:
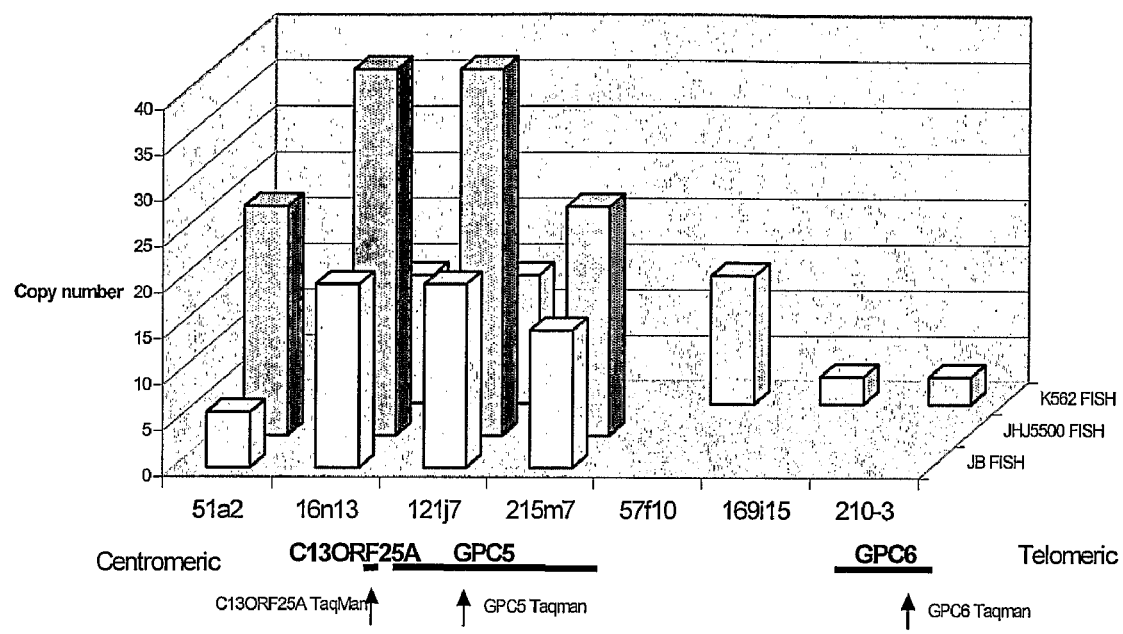
FIG. 1: FISH results using BACs spanning the amplified 13q31q32 region in two primary RMS samples and the cell line K562. The minimal region of amplification is defined by RP11-51a2 at the centromeric end and by GPC6 Taqman at the telomeric end which shows no amplification. Therefore, the region of minimal amplification flanks the GPC5 gene but does not extend into the next telomeric gene GPC6. The gene C13ORF25A, located proximally centromeric to GPC5, has been suggested to be implicated in lymphoma (33).

The glypicans are cell surface heparan sulphate proteoglycan (HSPG) molecules which consist of a protein core carrying heparan sulphate (HS) glycosaminoglycan chains and linked to the plasma membrane of the cell through a GPI anchor. For general reviews see Perrimon and Bernfield (2000) Nature 404: 725-728 and Selleck (1999) Am J Hum Genet 64: 372-377.

The HS chains themselves are attached to the serine residues of consensus SGXG "glycanation" sites. They each consist of a tetrasaccharide linker (-GlcA-Gal-Gal-Xyl) to which is added a linear polymer of a repeating disaccharide unit made up of GlcNac and GlcA. After the chains have been synthesized, they are subjected to processing in the Golgi by the enzymes N-deacetylase/N-sulphotransferase (NDST), uronosyl C5-epimerase, 2-O-sulphotransferase (2-OST), 6-O-sulphotransferase (6-OST) and 3-O-sulphotransferase (3-OST).

The HSPGs are increasingly thought to play specific roles in cell signaling. Some HSPGs may act as co-receptors for growth factor signaling (see the reviews by Perrimon and Bernfield, and Selleck, above). Glypican-3 has been shown to co-immunoprecipitate with FGF2 and BMP-7 (Int J Cancer 2003 103:455-65), while glypican-1 has been shown to co-immunoprecipitate with FGF2 and HB-EGF and to increase the growth stimulatory action of these growth factors (a Clin Invest 1998 102(9) 1662-73). Glypican-4 modulates the function of FGF2 by suppressing its growth stimulatory properties (Dev Dyn 219(3):353-67).

The mRNA and protein sequence of human GPC5 is found in Veugelers et al "Characterization of Glypican-5 and chromosomal localization of human Glypican-5; new member of glypican gene family" Genomics 1997 40(1):24-30. The genomic structure of the gene is described in Veugelers et al "A 4 MB BAC/PAC contig+complete genomic structure of the GPC5/GPC6 gene cluster on chromosome 13q32" Matrix Biol 2001 20(5-6):375-85. The GenBank reference sequence accession number is AF001462 (gi:3015541) for mRNA and NP004457 for protein. Homologous proteins have also been identified in mouse (NP 780709) and rat (XP 224489) having protein sequence identity of 82% and 87% respectively to the human sequence. This is greater than the next most homologous gene within the human genome GPC3 (NP 004475) which has a protein sequence identity of 46% with human GPC5.

"GPC5 protein" is used herein as a general term to include both the core protein and/or its associated heparan sulphate chains. References to the protein should be construed accordingly.

Cells

The term "cancer cell" is used throughout this specification to refer to any transformed cell including cells from cancers and tumours occurring in vivo, as well as laboratory cell lines adapted to continuous culture. Such cell lines typically display characteristics such as unlimited capacity for in vitro replication, loss of contact inhibition, ability to form tumours in animals, etc. They may historically be derived from a cancer, or may have been transformed in the laboratory.

The cell may be of any suitable species, although mammalian cells are preferred. Particularly preferred are human and rodent (e.g. mouse or rat) cells.

Target cells of the various methods described typically overexpress GPC5. The cells may have been engineered to overexpress GPC5, e.g. by transformation with a vector comprising nucleic acid encoding GPC5, or may naturally overexpress GPC5, in that they overexpresses GPC5 without having been deliberately manipulated to do so.

A cell is considered to overexpress GPC5 if it shows a higher level of RNA or protein than normally found in that cell type. A tumour cell may be considered to overexpress GPC5 if it shows a level of expression greater than that found in a corresponding cell type from which the tumour is thought to be derived. For example, RMS cells can be compared to normal muscle cells or muscle precursor cells, breast cancer cells to healthy breast tissue or normal breast epithelial cells and prostate cancer cells to healthy prostate tissue or normal prostate epithelium.

Thus a cell type which does not normally express GPC5 may be considered to overexpress, or inappropriately express, GPC5 if it shows a detectable level of GPC5 expression A cell which would normally show detectable GPC5 expression may be considered to overexpress GPC5 if it shows double the normal level of RNA or protein for that cell type, more preferably 5 times, 10 times, 50 times or 100 times the normal level for that cell type. The brain is the only normal human adult tissue which has been reported to display detectable expression of GPC5.

The same considerations, mutatis mutandis, apply to determining whether whole tissues, body fluids etc. display elevated levels of GPC5.

WT1 is normally only expressed in specific cell types in kidney, gonads, haematopoietic and nervous system, and mesothelium (Reddy, J. C., and Licht, J. D. (1996) *Biochim Biophys Acta* 1287, 1-28). Overexpression of WT1 in these tissues or cancers derived therefrom may be determined as described above for GPC5. Expression in other cell types may be considered inappropriate.

Antagonists

The term "GPC5 antagonist" encompasses two different classes of agent.

An "antagonist of GPC5 activity" is an agent which prevents the mature GPC5 protein from exerting its normal function when expressed at the cell surface. Typically these will be binding agents for GPC5 protein which are capable of binding to GPC5 protein (core protein and/or HSPG chains) and inhibiting its pro-proliferative function.

An "antagonist of GPC5 expression" is an agent capable of inhibiting or blocking expression of the mature protein at the cell surface, although it will be appreciated that the ultimate effect of such agents is also to inhibit GPC5 function or activity.

GPC5 antagonists may therefore be identified by screening candidate compounds or substances for the ability to bind GPC5. Suitable assay methods are described below.

Those candidates which show suitable binding may be screened (subsequently or in parallel) for their ability to inhibit proliferation of a cell overexpressing GPC5. Suitable cells include those which naturally overexpress GPC5 (such as cell lines derived from GPC5-overexpressing cancers), as well as those engineered to overexpress GPC5 (e.g. by transformation with a vector encoding GPC5).

By contrast, antagonists of GPC5 expression typically comprise nucleic acid molecules capable of hybridizing to GPC5 genomic DNA, precursor mRNA, mRNA, or cDNA, which may be single stranded or double stranded. Such modulators include antisense RNA or DNA, triple helix-forming molecules, RNAi, siRNA and ribozymes. (Such antagonists may also be considered to be GPC5 binding agents as described below.) Nucleic acids comprising chemically modified nucleotides (such as locked nucleic acids, or propynyl, methyl or G-clamped pyrimidine nucleotides) as well as nucleic acid analogues having modified sugar residues (e.g. 2'-o-methyl and 2'-methoxyethyl modifications) or backbone structure (e.g. by incorporation of phosphoramidite or morpholino linkages, or peptide nucleic acids (PNAs)) are also included within this definition. For more details of these modifications and antisense techniques in general, see Dean and Bennett (2003) Oncogene 22: 9087-9096 and references cited therein.

Antisense oligonucleotides hybridize with complementary sequences of RNA generally by Watson-Crick base pairing. The resultant double stranded complex prevents translation of the message into protein product either by steric blocking at the ribosome or activation of RNase H that cleaves the RNA strand of the duplex. With respect to antisense DNA, oligodeoxy-ribonucleotides derived from the translation initiation site, e.g. between the −10 and +10 regions of the target gene nucleotide sequence of interest, are preferred.

In using antisense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene.

The complete sequence corresponding to the coding sequence need not be used. For example fragments of sufficient length may be used. It is a routine matter for the person skilled in the art to screen fragments of various sizes and from various parts of the coding sequence to optimize the level of antisense inhibition. It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than 500 nucleotides are preferable where possible.

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridize. There may be down regulation of gene expression even where there is about 5%, 10%, 15% or 20% or more mismatch between the sequence used and the target gene.

Double stranded RNA (dsRNA) has been found to be even more effective in gene silencing than antisense strands alone (Fire A. et al Nature, Vol 391, (1998)). dsRNA mediated silencing is gene specific and is often termed RNA interference (RNAi). RNA interference is a two step process. First, dsRNA is cleaved within the cell to yield short interfering RNAs (siRNAs) of about 21-23 nt length with 5' terminal phosphate and 3' short overhangs (~2 nt) The siRNAs target the corresponding mRNA sequence specifically for destruction (Zamore P. D. Nature Structural Biology, 8, 9, 746-750, (2001) RNAi may be also be efficiently induced using chemically synthesized siRNA duplexes of the same structure with 3'-overhang ends (Zamore P D et al Cell, 101, 25-33, (2000)). Synthetic siRNA duplexes have been shown to specifically suppress expression of endogenous and heterologous genes in a wide range of mammalian cell lines (Elbashir SM. et al. Nature, 411, 494-498, (2001)). See also Fire (1999) Trends Genet. 15: 358-363, Sharp (2001) Genes Dev. 15: 485-490, Hammond et al. (2001) Nature Rev. Genes 2: 1110-1119 and Tuschl (2001) Chem. Biochem. 2: 239-245.

Ribozymes are enzymatic RNA molecules capable of catalyzing the specific cleavage of RNA. (For a review, see Rossi, J., 1994, Current Biology 4: 469-471). The mechanism of ribozyme action involves sequence specific hybridization of the ribozyme molecule to complementary target RNA, followed by an endonucleolytic cleavage. The composition of ribozyme molecules must include one or more sequences complementary to the target protein mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target proteins.

Specific ribozyme cleavage sites within any potential RNA target are initially identified by scanning the molecule of interest for ribozyme cleavage sites which include the following sequences, GUA, GUU and GUC. Once identified, short sequences of between 15 and 20 ribonucleotides corresponding to the region of the target protein gene containing the cleavage site may be evaluated for predicted structural features, such as secondary structure, that may render the oligonucleotide sequence unsuitable. The suitability of candidate sequences may also be evaluated by testing their accessibility to hybridize with complementary oligonucleotides, using ribonuclease protection assays.

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementary to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

WT1 antagonists are agents which prevent WT1 exerting its function as a transcription factor. As it is an intracellular protein, preferred WT1 antagonists are those which interfere with WT1 expression. Particularly preferred WT1 antagonists comprise nucleic acid sequences complementary to the sequence of WT1 mRNA or pre-mRNA. These include antisense RNA, dsRNA molecules (including RNAi and siRNA), and ribozymes. For exemplary WT1 sequences, see GenBank accession numbers NM_000378.2, NM_024426.2, NM_024425.1, NM_024424.1. All accession numbers cited in this application are taken from GenBank release 140.0, updated 20 Feb. 2004.

Binding agents

In most aspects of the invention, GPC5 binding agents are referred to in the context of agents capable of binding to GPC5 core protein and/or its associated heparan sulphate chains. However in some aspects of the invention, such as the diagnostic methods described below, agents capable of binding to nucleic acid encoding GPC5, and in particular to GPC5 pre-mRNA, mRNA, or cDNA derived therefrom, may also be considered to be GPC5 binding agents.

In preferred embodiments the binding agents which are used may be regarded to constitute a specific binding pair with GPC5.

The term "specific binding pair" may be used to describe a pair of molecules comprising a specific binding member (sbm) and a binding partner (bp) therefor which have particular specificity for each other and which in normal conditions bind to each other in preference to binding to other molecules. Examples of specific binding pairs are antigens and antibodies, ligands (such as hormones, etc.) and receptors, avidin/ streptavidin and biotin, lectins and carbohydrates, and complementary nucleotide sequences.

By "specific" is meant that the particular binding sites of the agent which interact with GPC5 will not show any significant binding to molecules other than GPC5 which are likely to be encountered by the binding agent (e.g. other molecules in an assay or on a given cell surface). For example the interaction between the binding agent and GPC5 may have a $K_D$ of the order of $10^{-6}$ to $10^{-9} M^{-1}$ or smaller.

The binding agent may bind to the protein core or the HS chains of the GPC5 molecule, but in preferred embodiments binds to the protein core, preferably to the hydrophilic regions of the core, e.g. to part or all of the sequence CKSYTQRVVGNGIKAQ (SEQ ID NO: 1)

The binding agent may be a protein or polypeptide of 50 amino acids in size or greater, or a peptide of up to 50 amino acids in length. Typically a peptide will be from 5 to 50 amino acids in length, more typically 10 to 20 amino acids in length. Alternatively the binding agent may be a small molecule e.g. of 1000 Da or less, preferably 750 Da or less, preferably 500 Da or less.

Antibodies are preferred examples of binding agents. Thus preferred assay formats for diagnosis are immunological assays including ELISA assays, and immunohistochemistry, which may be carried out on whole cells or tissue sections, other forms of immunostaining for FACS analysis, confocal microscopy or the like, which may be carried out on single cells or populations of dispersed cells, and immunoblotting, which is suitable for analysis of cell extracts.

It has been shown that fragments of a whole antibody can perform the function of binding antigens. The term "antibody" is therefore used herein to encompass any molecule comprising the binding fragment of an antibody. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding member (Bird et al, Science, 242, 423-426, 1988; Huston et al, PNAS USA, 85, 5879-5883, 1988).

Diagnostic Methods and Other Assays

As well as being useful as GPC5 antagonists and targeting agents, binding agents for GPC5 may also be used to detect the presence of GPC5 in biological samples. This has a number of applications within the scope of the invention.

The binding agents described herein may be used to assess the susceptibility of a particular cancer to treatment with GPC5 antagonists or binding agents by assessing the level of expression of GPC5 in that cancer. A cancer found to overexpress or have an elevated level of GPC5 may be treatable by means of the methods and compositions described herein.

The method typically comprises contacting a sample with a GPC5 binding agent, the sample having been isolated from a subject suffering from the cancer in question. The sample may comprise one or more whole cells or extracts of cells, and may be derived from any suitable biological sample suspected or known to contain one or more cancer cells. Examples include tissue samples (e.g. biopsies) and samples of body fluid, e.g. blood, serum or plasma.

The binding agent may detect expression of either GPC5 protein or mRNA.

In preferred embodiments the method further comprises comparing the level of GPC5 expression with that found in one or more reference samples, which may be pre-determined. Suitable reference samples include samples of the same tissue type, or a comparable tissue type, as that from which the cancer or suspected cancer is derived. The reference samples may be obtained from the same individual as the test sample, or from different individuals. The reference samples may also include samples of cancer cells of known type, optionally of known GPC5 expression level, which may serve as positive controls.

The sample may be derived from a cancer previously identified to inappropriately express or overexpress WT1. Alternatively the method may further comprise the step of determining the level of expression of WT1 to see whether combined therapy with one or more WT1 antagonists would be beneficial.

The invention also provides methods of determining whether a subject is suffering from a cancer characterized by overexpression of GPC5, the method comprising contacting a sample from the subject with a GPC5 binding agent. Preferably the method comprises determining the level of circulating free (i.e. not cell-associated) GPC5. In such cases, the sample is preferably blood, serum or plasma, and the binding agent detects GPC5 protein.

Again, the results obtained may be compared with suitable positive and/or negative control samples to arrive at an indication of the subject's clinical status.

Methods for determining the concentration of analytes in samples from individuals are well known in the art and readily adapted by the skilled person in the context of the present invention to determine expression of GPC5 protein or mRNA as appropriate. Such assays may allow a physician to optimize the treatment of a disorder and, thus, the methods described allow for planning of appropriate therapy, permitting stream-lining of treatment by targeting those most likely to benefit.

Assay methods for determining, the concentration of protein markers typically employ binding agents having binding sites capable of specifically binding to protein markers, or fragments thereof, or antibodies in preference to other molecules. Examples of binding agents include antibodies, receptors and other molecules capable of specifically binding the analyte of interest. Conveniently, the binding agents are immobilized on a solid support, e.g. at defined, spatially separated locations, to make them easy to manipulate during the assay.

The sample is generally contacted with the binding agent(s) under appropriate conditions which allow the analyte in the sample to bind to the binding agent(s). The fractional occupancy of the binding sites of the binding agent(s) can then be determined either by directly or indirectly labelling the analyte or by using a developing agent or agents to arrive at an indication of the presence or amount of the analyte in the sample. Typically, the developing agents are directly or indirectly labelled (e.g. with radioactive, fluorescent or enzyme labels, such as horseradish peroxidase) so that they can be detected using techniques well known in the art. Directly labelled developing agents have a label associated with or coupled to the agent. Indirectly labelled developing agents may be capable of binding to a labelled species (e.g. a labelled antibody capable of binding to the developing agent) or may act on a further species to produce a detectable result. Thus, radioactive labels can be detected using a scintillation counter or other radiation counting device, fluorescent labels using a laser and confocal microscope, and enzyme labels by the action of an enzyme label on a substrate, typically to produce a colour change. In further embodiments, the developing agent or analyte is tagged to allow its detection, e.g. linked to a nucleotide sequence which can be amplified in a PCR reaction to detect the analyte. Other labels are known to those skilled in the art are discussed below. The developing agent(s) can be used in a competitive method in which the developing agent competes with the analyte for occupied binding sites of the binding agent, or non-competitive method, in which the labelled developing agent binds analyte bound by the binding agent or to occupied binding sites. Both methods provide an indication of the number of the binding sites occupied by the analyte, and hence the concentration of the analyte in the sample, e.g. by comparison with standards obtained using samples containing known concentrations of the analyte.

In alternative embodiments, the analyte can be tagged before applying it to the support comprising the binding agent.

Preferred formats are ELISA assays and immunostaining (e.g. immunohistochemistry).

There is also an increasing tendency in the diagnostic field towards miniaturization of such assays, e.g. making use of binding agents (such as antibodies or nucleic acid sequences) immobilized in small, discrete locations (microspots) and/or as arrays on solid supports or on diagnostic chips. These approaches can be particularly valuable as they can provide great sensitivity (particularly through the use of fluorescent labelled reagents), require only very small amounts of biological sample from individuals being tested and allow a variety of separate assays can be carried out simultaneously. This latter advantage can be useful as it provides an assay employing a plurality of analytes to be carried out using a single sample. Examples of techniques enabling this miniaturized technology are provided in WO84/01031, WO88/1058, WO89/01157, WO93/8472, WO95/18376/WO95/18377, WO95/24649 and EP 0 373 203 A. Thus, in a further aspect, the present invention provides a kit comprising a support or diagnostic chip having immobilized thereon a plurality of binding agents capable of specifically binding different protein markers or antibodies, optionally in combination with other reagents (such as labelled developing reagents) needed to carrying out an assay. In this connection, the support may include binding agents specific for analytes such as vimentin, e.g. as disclosed in U.S. Pat. No. 5,716,787.

Such assay methods may also be used to screen for binding agents capable of binding to GPC5 protein. Candidate agents identified by such screens may be subjected to one or more rounds of modification and re-testing in order to identify further agents having improved properties. The skilled person will be aware of numerous suitable screening methods and will be able to design appropriate protocols for identification of candidate binding agents.

Alternatively the binding agent may be a nucleic acid molecule capable of binding to mRNA or precursor mRNA. Thus mRNA or precursor mRNA encoding GPC5 may be detected by hybridization with a probe having a suitable complementary sequence, e.g. by Northern blotting or in situ hybridization. Such protocols may use probes of at least about 20-80 bases in length. The probes may be of 100, 200, 300, 400 or 500 bases in length or more. Binding assays may be conducted using standard procedures, such as described in Sambrook et al., Molecular Cloning A Laboratory Manual (New York: Cold Spring Harbor Laboratory Press, 1989 or later editions).

Alternatively, conventional RT PCR procedures (including quantitative PCR procedures) may be used to analyze the presence or amount of mRNA or precursor mRNA in a given sample. A suitable primer having at least 15 to 20 bases complementary to the GPC5 mRNA or precursor mRNA sequence will typically be used to prime cDNA synthesis. Subsequently, a segment of the cDNA is amplified in a PCR reaction using a pair of nucleic acid primers. The skilled person will be able to design suitable probes or primers based on the publicly available sequence data for GPC5 (see above).

Whether it is a protein, peptide, small molecule or nucleic acid, the binding agent may also act as an antagonist of GPC5.

Pharmaceutical Compositions

GPC5 antagonists and binding agents can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes or topical application.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Suitable carriers, adjuvants, excipients, etc. can be found in standard pharmaceutical texts, for example Remington's Pharmaceutical Sciences, 20th Edition, 2000, pub. Lippincott, Williams & Wilkins; and Handbook of Pharmaceutical Excipients, 2nd edition, 1994.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, eg in a viral vector (a variant of the VDEPT technique—see below). The vector could be targeted to the specific cells to be treated, or it could contain regulatory elements which are switched on more or less selectively by the target cells. The targeting method may itself make use of the expression of GPC5 on the surface of the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

A composition may be administered alone or in combination with other treatments, either simultaneously or sequentially dependent upon the condition to be treated.

Expression of GPC5 in healthy adult human tissue is largely restricted to the brain. Therefore when designing pharmaceutical and other compositions for in vivo administration according to the invention, it may be desirable to make use of components (and particularly active ingredients) which tend not to cross the blood-brain barrier.

The blood-brain barrier is most permeable to small (up to approx. 700 Da) and/or lipophilic molecules such as water, carbon dioxide, oxygen and anaesthetic molecules, while being almost impermeable to plasma proteins and non-lipid-soluble large organic molecules. It may therefore be preferable that the compositions of the invention comprise GPC5 antagonists and/or binding agents which are relatively hydrophilic, and/or above at least 1 kDa. Peptides and proteins may be preferred. Strategies for screening and design of GPC5 binding agents and antagonists may be designed accordingly.

Gene Therapy

Nucleic acids encoding modulators (antagonists) of GPC5 expression (e.g. antisense, RNAi, siRNA or ribozyme molecules) may be used in methods of gene therapy. A construct capable of expressing such nucleic acid may be introduced into cells of a recipient by any suitable means, such that the relevant sequence is expressed in the cells.

The construct may be introduced in the form of naked DNA, which is taken up by some cells of animal subjects, including muscle cells of mammalians. In this aspect of the invention the construct will generally be carried by a pharmaceutically acceptable carrier alone. The construct may also formulated in a liposome particle, as described above.

Such methods of gene therapy further include the use of recombinant viral vectors such as adenoviral or retroviral vectors which comprise a construct capable of expressing a polypeptide of the invention. Such viral vectors may be delivered to the body in the form of packaged viral particles. The viral vectors may themselves be targeted to the appropriate cells via GPC5 binding agents.

Constructs of the invention, however formulated and delivered, will be for use in treating tumours in conjunction with therapy. The construct will comprise the relevant nucleic acid linked to a promoter capable of expressing it in the target cells. The constructs may be introduced into cells of a human or non-human mammalian recipient either in situ or ex-vivo and reimplanted into the body. Where delivered in situ, this may be by for example injection into target tissue(s) or in the case of liposomes, inhalation.

Gene therapy methods are widely documented in the art and may be adapted for use in the expression of the required sequence.

Materials And Methods

Patient Samples and Cell Lines

Samples were collected from patients with a diagnosis of RMS from the Royal Marsden NHS Trust or participating UKCCSG (United Kingdom Children's Cancer Study Group) centres around the time of first diagnosis. In addition, 22 samples were collected at the University hospital in Leuven, Belgium and two samples were collected from University hospital Dusseldorf. Samples were snap frozen and material taken adjacent to samples were taken to confirm high tumour content. A pathological diagnosis of RMS was made in the majority of cases by the pathological review committee of the MMT studies. In cases where there was no central review of pathology, morphology and immunohistochemistry reports were examined to ensure RMS pathology. The diagnosis of ARMS was consistent with the current histopathological criteria whereby any alveolar foci are sufficient to result in ARMS classification. Clinical data for the majority of tumours were obtained from the UKCCSG data centre (Leicester, UK) otherwise data was collected directly from participating hospitals. Only patients under the age of 21 were used in survival analysis. The majority of patients were treated using the SIOP (Societe Internationale de Oncologie Paediatrique) MMT89 (Malignant Mesenchymal Tumour) protocol or the closely related MMT95 and MMT98 protocols. Some patients were treated using local treatment protocols that were comparable to the MMT protocols. Tumour samples from breast and prostate cancer patients were snap frozen after removal. DNA and RNA was extracted from samples as previously described (20). K562 cl.6 cells, a subclone of the parent erythroleukaemia were kindly provided by Professor Adrian Newland and Dr Xu-Rong Jiang, (The London Hospital Medical College, UK) and the RMS cell line T91-95 used in the transfection studies was a kind gift from Jaclyn Biegel (Children's Hospital of Philadelphia).

Chromosomal Level Data on Genetic Imbalances and Differential Expression

Data from previous studies on RMS included comparative genomic hybridization (CGH) analysis for genomic imbalances (n=127) (4-10)(unpublished data) and comparative expressed sequence hybridization (CESH) data for chromosomal level differential expression (n=45)(19, 20). These data were used here to compare the genomic changes with differential expression relative to muscle at 13q31-q32.

Fluorescence In Situ Hybridization—FISH

Interphase fluorescence in situ hybridization (FISH) was performed as described previously (21). We used touch preps from two ARMS primary samples and the K562 cell line which possess a 13q31-32 amplicon. BAC (Bacterial Artificial Chromosome) clones spanning the 13q31-32 region were obtained from the Sanger Centre and included RP11-51a2, RP11-16n13, RP11-121J7, RP11-215m7, RP11-57f10, RP11-169i15, RP11-210-3.

Real Time Quantification of GPC5/6 DNA and RNA Levels

Five sets of primers and probes were designed in order to measure the amount of genomic and mRNA copies of GPC5 and GPC6 (see Table 1). All primers and probes were designed in accordance with Applied Biosystems' TaqMan® standard requirements. Primers and a probe were designed within intron 2 of the GPC5 gene to detect genomic copies of GPC5. To detect copies of GPC6 primers and a probe were designed within exon 3. So as to correct for aneuploidy the gene GJB2 was chosen as an endogenous control. GJB2 is a gene that is not believed to be involved in tumorigenesis and located in a region of chromosome 13 (13q11) not frequently altered in RMS. Primers and a probe were designed within exon 1.

To measure the amount of mature mRNA copies of GPC5 and GPC6 the probe was designed across the exon 1-exon 2 boundary and the exon 7-exon 8 boundary respectively. Applied Biosystems' Predeveloped GAPDH (Glyceraldehyde 3-phosphate dehydrogenase) was used as an endogenous control. 25 µL multiplex PCR reactions were run using 2× Universal TaqMan® Master Mix (Applied Biosystems Pt No. 4304437), the concentration of primers and probes shown in Table 1 and 10 ng of DNA or cDNA. These samples were run in triplicate under standard operating conditions on an ABI7700 SDS TaqMan® Machine (Applied Biosystems, CA). Limiting primer conditions were determined and template titrations showed that the comparative method was appropriate for both genomic and expression reactions (data not shown). Thus, the amount of GPC5 and GPC6 was measured relative to either normal genomic DNA in the case of genomic measurements and to normal muscle in the case of expression measurements. Normal genomic DNA was extracted from the blood of a healthy donor, normal muscle cDNA was produced from RNA extracted from a pool of 11 normal muscle biopsies.

Statistics

All statistics tests were performed using the SPSS 10.0 package and tested to the 5% significance level. Failure free survival was defined as the time from diagnosis to relapse, progression, death or if event free to the date of last contact. Time to death was defined as the time from diagnosis to death or if event free to the date of last contact.

Real Time Quantification of WT1 mRNA Levels

The primer pair and probe for the quantification of WT1 were designed using the Primer Express program (Applied Biosystems) according to the recommended guidelines and as described above.: WT1—Forward primer, 5'-TACCCAG-GCTGCAATAAGAGATATTTTAAG-3', reverse primer, 5', CCTTTGGTGTCTTTTGAGCTGGTC-3', and probe, 5'-CACTGGTGAGAAACCATACCAGTGT-GACTTCAAGGACT-3'. Each assay sample was analyzed in triplicate as above, and multiplexed to facilitate the measurement of gene expression levels relative to GAPDH (in vivo tumour samples) or 18 s ribosomal RNA expression (ribosomal RNA control reagents, Applied Biosystems) (in vitro cell line samples) using the standard curve method.

Polyclonal Antibody Production, Purification and Western Blotting

As no commercial antibody existed for GPC5 a custom polyclonal antibody was raised to the epitope peptide H2N-CKSYTQRVVGNGIKAQ —COOH (16aa) by immunizing two rabbits (performed by Eurogentec, Belgium). 5 mg of epitope peptide was immobilized to 8 ml of SulfoLink coupling Gel (Pierce Biotechnology, IL) and used to affinity purify final bleed serum from the rabbit with the highest antibody titre. Antibody specificity was confirmed by western blotting, performed as previously described (22), using 2 µL of a GPC5 in vitro translation reaction and 2 µL of a luciferase in vitro translation reaction as a control. A single clean band of the correct size was obtained for GPC5. Membrane protein was extracted from cell lines using MEM-PER extraction reagent (Pierce Biotechnology, IL) ultra-filtered using YM-30 Filter (Millipore) to remove detergent and the protein concentration determined using the BCA assay kit (Pierce Biotechnology, IL).

TABLE 1

Primers and Probes

Primers and Probes for Genomic Quantification of GPC5

| | | |
|---|---|---|
| GPC5 Forward 5'-CCCACCCAAATCTCATCTAGAATT-3' | (SEQ ID NO: 5) | 300 nM |
| GPC5 Probe- 5'-CCGGGTTCCTCCCTTTGCACATG-3' FAM Labelled | (SEQ ID NO: 6) | 100 nM |
| GPC5 Reverse 5'-ACGCATTGCCCAGTTGTTAGA-3' | (SEQ ID NO: 7) | 300 nM |
| GJB2 Forward 5'-TGGTTGCATTTAAGGTCAGAATCTT-3' | (SEQ ID NO: 8) | 50 nM |
| GJB2 Probe- 5'-CTAGCGACTGAGCCTTGACAGCTGAGC-3' Vic Labelled | (SEQ ID NO: 9) | 100 nM |
| GJB2 Reverse 5'-GCAGAGGCACGTTCAGGAA-3' | (SEQ ID NO: 10) | 300 nM |

TABLE 1-continued

Primers and Probes

Primers and Probes for Expression Quantification of GPC5

| | | |
|---|---|---|
| GPC5 Forward 5'-GGGCTGCCGGATTCG-3' | (SEQ ID NO: 11) | 300 nM |
| GPC5 Probe- 5'-CGCGGGCAGGACCTGATCTTCA-3' FAM Labelled | (SEQ ID NO: 12) | 100 nM |
| GPC5 Reverse 5'-CTGGTGCAACATGTAGGCTTTT-3' | (SEQ ID NO: 13) | 300 nM |
| GAPDH PDAR Applied Biosystems Part No. 4310884E | | 1X |

Primers and Probes for Genomic Quantification of GPC6

| | | |
|---|---|---|
| GPC6 Forward 5'-TGACCAGCTCAAGCCATTTG-3' | (SEQ ID NO: 14) | 50 nM |
| GPC6 Probe- 5'-AGACGTGCCCCGGAAACTGAAGATTC-3' FAN Labelled | (SEQ ID NO: 15) | 100 nM |
| GPC6 Reverse 5'-TGAAGGCGCGGGTAACC-3' | (SEQ ID NO: 16) | 300 nM |

Primers and Probes for Expression Quantification of GPC6

| | | |
|---|---|---|
| GPC6 Forward 5'-AACGAGGAGGAATGCTGGAA-3' | (SEQ ID NO: 17) | 300 nM |
| GPC6 Probe- 5'-CACAGCAAAGCCAGATACTTGCCTGAGATC-3' FAN Labelled | (SEQ ID NO: 18) | 100 nM |
| GPC6 Reverse 5'-CTGGTTGGTGAGCCCATCAT-3' | (SEQ ID NO: 19) | 50 nM |

Primers for amplification of GPC5 sequence including restriction sites and kozak sequence

| | | |
|---|---|---|
| GPC5 Forward 5'-TATAAGCTTCCACCATGGACGCACAGACCTGGCCCG-3' | (SEQ ID NO: 20) | 300 nM |
| GPC5 Reverse 5'-CGCGTCGACTTACCAAATCCCGGGAAGTA-3' | (SEQ ID NO: 21) | 300 nM |

Antisense Oligonucleotides (ASOS) Targeted to GPC5 and WT1.

20 mer, 2'-O-methoxyethyl (2'-M0E) chimeric oligonucleotides consisting of a central window of eight 2'-deoxy unmodified sugar residues with flanking 2'-MOE regions and a fully thioated backbone were synthesized by Isis Pharmaceuticals Inc., as described previously (Baker, B. F., Lot. S. S., Condon, T. P., Cheng-Flournoy, S., Lesnik, E. A., Sasmor, H. M., and Bennett, C. F. (1997) *J Biol Chem* 272, 11994-12000). Twenty antisense oligonucleotides targeting predicted accessible GPC5 mRNA sequences over the full length mRNA product were provided and screened for activity in K562 cells. ISIS 15770, sequence 5'-ATGCATTCTGC-CCCCAAGGA-3' (SEQ ID NO: 22), a 5-10-5 gapmer targeting murine c-raf kinase was used as a control in this screen. The two active compounds identified were ISIS 276107 sequence 540 -CAGCCCCCTGACAGCTCCCA-3' (SEQ ID NO: 23), and ISIS 276119 sequence 5'-CCATCTGCAG-CAGCTAATTC-3' (SEQ ID NO: 24). Also used as a control was ISIS 276124, sequence 5'-TGGATTTGCTTTACACAT-CACT-3' (SEQ ID NO: 25)

The previously identified WT1 ASOs were ISIS 16609, sequence 5' -GCCCCTTCTGTCCATTTCACT-3' (SEQ ID NO: 26), targeting WT1 exon 5 (ASWT1 exon 5) and ISIS 16601, sequence 5'-CACATACACATGCCCTGGCC-3' (SEQ ID NO: 27), targeting the 3'-UTR region of WT1 (ASWT13'UTR). The control ASO was ISIS 105730, sequence 5'-CCATCGACCTGCACCGATCA-3' (SEQ ID NO: 28), a scrambled sequence of ASWT13'UTR, (ASWT1 scram).

Assessment of GPC5 and WT1 Antisense Activity.

Antisense or control oligonucleotides were dissolved in PBS and introduced into K562 cells by low voltage electroporation: 40 µl of appropriately diluted ASOs were combined with 360 µl of cell suspension at $2 \times 10^7$ cells/ml and cells were electroporated (Bio-Rad Gene Pulser® II Electroporation system with Pulse Controller Plus capacitance extender accessory module, Bio-Rad Laboratories Ltd, Hemel Hempstead, Herts, UK) using 300V and a capacitor value of 1000 µF, and diluted to 10 ml with complete medium. From each sample appropriate duplicate aliquots of cells were serially diluted in complete medium for assessment of cytotoxicity while the remaining cells were incubated at 37° C. for 24 hours ana RNA extracted for quantification of GPC5 and/or WT1 expression levels.

Clonogenic Cell Survival Assay.

In this assay, cells are grown at low density in suspension in soft agar following treatment. Each colony formed derives from a single surviving cell. 2 ml aliquots of diluted cells were added to polystyrene tubes (Elkay Products (UK) Ltd., Basingstoke, Hampshire, UK) containing 3 ml of medium supplemented with 20% FCS and 0.2% Agar Noble (DIFCO Laboratories, Detroit, Mich.), incubated at 37° C., and colonies containing at least 32 cells counted after 14 days. The number of colonies formed following drug treatment were compared to the number obtained following sham electroporation or a control scrambled oligonucleotide and expressed as % control treatment. In a number of separate experiments, control plating efficiencies ranged from 22-38%, with 800-1600 cells typically plated. In addition, cells from the dilution series (approx $10^3$-$10^4$ cells/ml) were allowed to grow up in suspension culture in parallel for 3-5 days in order to confirm cytotoxicity.

Production of GPC5 Construct and Transfection

Image clone 5744533 containing the full coding region of human GPC5 was obtained from the ATCC (American Type Culture Collection at LGC Promochem, UK). The coding region was amplified using the Xpand High fidelity PCR kit (Roche, Switzerland) and primers to produce a product containing an in frame kozak sequence at the 5' end (see Table 1). This product was TA cloned into the vector pCR4-TOPO (Invitrogen, Calif.) and sequence confirmed using Applied Biosystems Big Dye Sequencing kit Version 1 and a 377 ABI Prism sequencing machine. The insert was restriction digested with EcoR1 and re-ligated into an EcoR1 digested vector pCMV-TnT (Promega, UK) using T4 DNA ligase (Invitrogen, Calif.). Purified pCMV-TnT-GPC5 and a control T7-luciferase plasmid were in vitro translated using Promega's Quick coupled TnT T7 in vitro translation system including biotin labelled lysine (Promega, UK) as per manufacturers instructions. Products were separated by SDS-PAGE, blotted onto Immoblion-P PVDF membrane (Millipore, UK) and colour developed using a streptavidin-Alkaline phosphatase and western blue colormetric substrate (Promega, UK) as per manufacturers instructions.

Following cleanup of plasmids using Wizard Purefection kit (Promega, UK) plasmids were transfected into the RMS cell line T91-95 at ~75% confluence using FuGene6 transfection reagent (Roche, Switzerland) in a ratio of 3 µl FuGene:1 µg DNA. pCMV-TnT-GPC5 was co-transfected in a molar ratio of 10:1 with pTK-Hyg (Clontech, Calif.). A control transfection using empty PCMV-TnT vector in a 10:1 molar ratio with pTK-Hyg was also performed. Cells were grown in Dulbecco's Modified Eagle Media (DMEM) and 10% foetal calf serum. 200 µg per ml of hygromycin (Clontech, Calif.) was added 48 hr post transfection in order to produce stable colonies. After two weeks healthy stable colonies were selected and expanded. Overexpression of GPC5 was confirmed by TaqMan RT-PCR using DNase treated cDNA (DNA Free, Ambion, Tex.) and increased protein was confirmed by western blot analysis.

Cell Proliferation Assay

In order to assess the growth characteristics of stably transfected cells a method based on the ability of the metabolic enzyme hexosaminidase to produce a coloured product by breaking down p-Nitrophenyl-N-acetyl-β-D-glucosaminide was used as previously described to measure cell numbers (23).

Results

Comparison of CGH and CESH Data

Meta-analysis of all the CGH data available in the literature showed that the region 13q31-32 was gained in 21/87 (25%) of ARMS and 9/40 (22%) of ERMS. 5/87 (6%) of the ARMS were defined as amplifying this region (4-10) (unpublished data). CESH analysis which detects gross differential expression on a region by region basis showed that 7/27 (26%) of ARMS and 4/19 (21%) of ERMS showed overexpression from 13q31-32 relative to normal muscle. Where CGH and CESH data was available from the same sample the majority of samples with gain at 13q31-32 also showed overexpression from the region 13q31-32 7/8 (88%). In addition, 3 samples showed overexpression from the region without any apparent gain by CGH.

Interphase FISH Analysis of 13q31-32 amplicon

Using BACs mapped to 13q31-32 it was possible to place the region of amplification in two primary RMS samples and the cell line K562 to a region of 13q31-32 approximately 3.8 Mb in length from ~88,200K to ~91,900K on the physical map (Build 32) of chromosome 13 (see FIG. 1). 2 Mb of this amplified region had the highest copy number in both RMS samples and this 2 Mb interval contains the gene GPC5 (Glypican 5). At ~2 Mb in length GPC5 is the second largest gene in the human genome to date (24). Amplification levels in K562 appeared lower and stopped short of GPC6 the next annotated gene telomeric of GPC5. In addition to GPC5, the only other curated genes within this amplified region are pseudogenes (www.ncbi.nlm.nih.gov/locuslink) and the recently-identified C13ORF25 (33). The FISH mapping of the 13q31-q32 amplification in 5 lymphoma samples by Yu et al defined a minimal amplification which spanned the same region but extended an extra 1 Mb centromeric of GPC5 (13).

Quantification of GPC5/GPC6 Genomic Copy Number and Expression

Genomic copy number of GPC5 was measured in primary tumour samples taken from 102 individuals with a diagnosis of RMS, of which 45 were ARMS, 51 were ERMS and 5 were RMS-Not Otherwise Specified (RMS-NOS). 13 out of 102 RMS (13%) show gain of GPC5 copies >1.5 times relative to normal DNA; by subtype 7/45 ARMS (16%), 6/51 ERMS (12%). The largest amplification showed ~90 times more genomic copies than normal genomic DNA. This data was concurrent with CGH and FISH data for samples where data was available (4). There was no significant difference between genomic copy number in ARMS and ERMS. All samples with gain of GPC5 copies were measured for their GPC6 copy number and showed no gain of genomic copy number.

Expression of GPC5 was measured in 85 individuals of which 42 were diagnosed ARMS, 39 were diagnosed ERMS and 4 were diagnosed RMS-NOS. Expression of GPC5 is consistently greater than normal muscle and spans several orders of magnitude; median =83.5 times greater than normal muscle (see FIG. 2A). Although expression in samples with GPC5 amplification is always in the top quartile, overexpression is also apparent in some samples without a GPC5 amplification. Consequently there is no significant correlation between copy number and expression. Furthermore, there is no significant difference in GPC5 expression between ERMS and ARMS: ARMS median =80.5 times greater than relative to normal muscle, ERMS median =126 times greater than normal muscle. GPC6 expression was virtually undetectable in all but one RMS sample tested.

Figure 2:
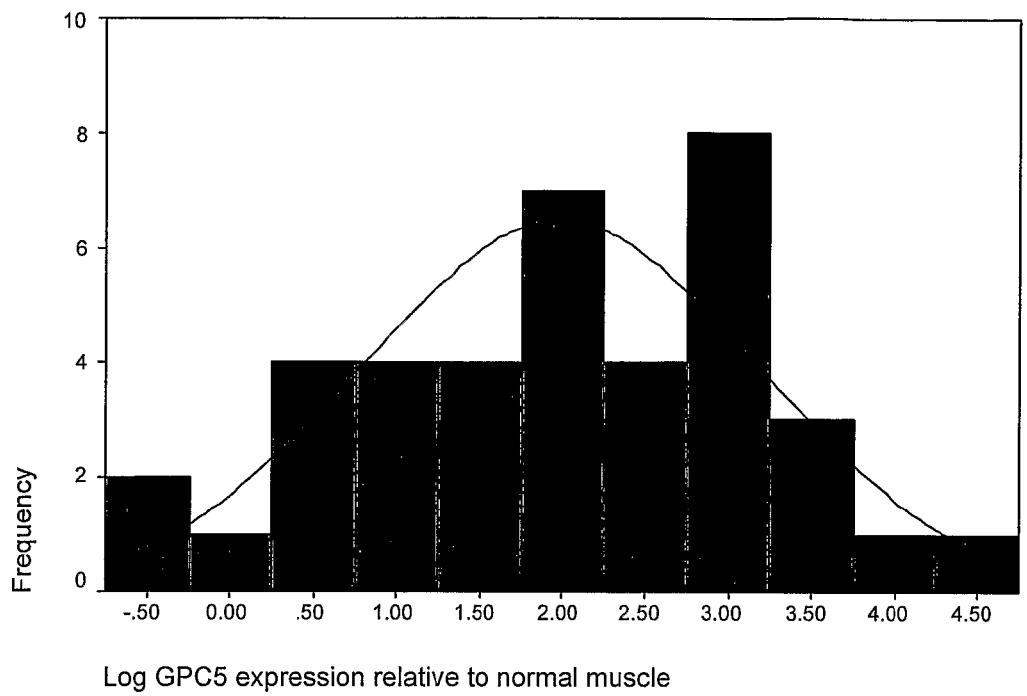
FIG. 2A: Log distribution of GPC5 expression relative to normal muscle; left (Embryonal), right (Alveolar).
FIG. 2B: Expression of C13ORF25A in rhabdomyosarcoma relative to normal muscle. Bars marked "A" indicate samples which show genomic amplification of C13ORF25A.
Figure 2:
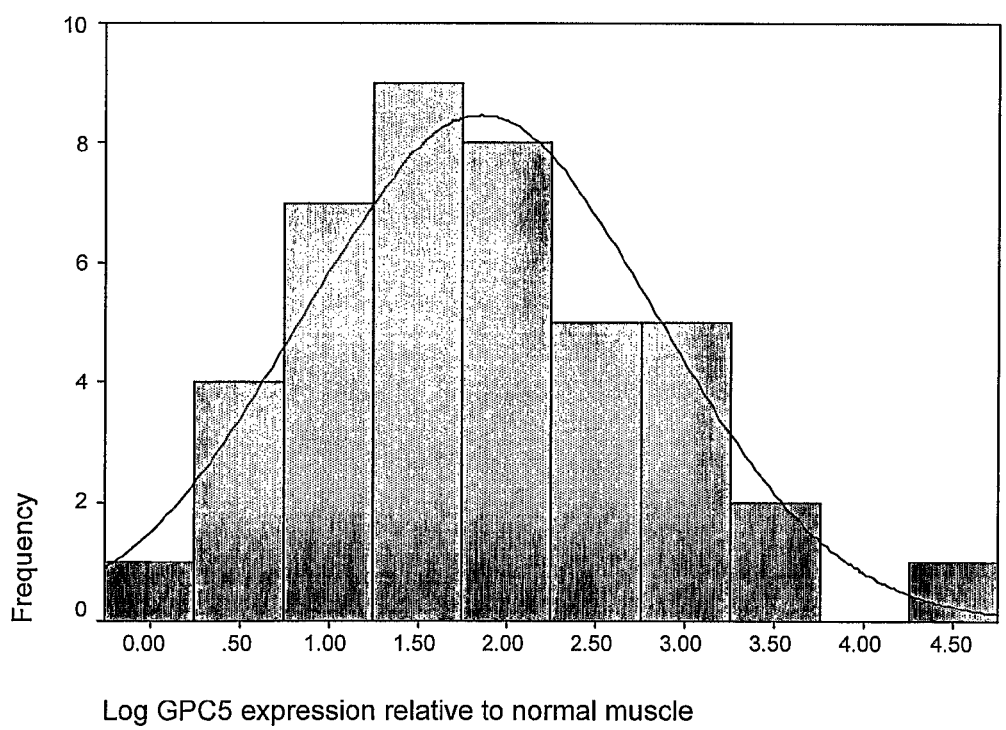
Figure 2:
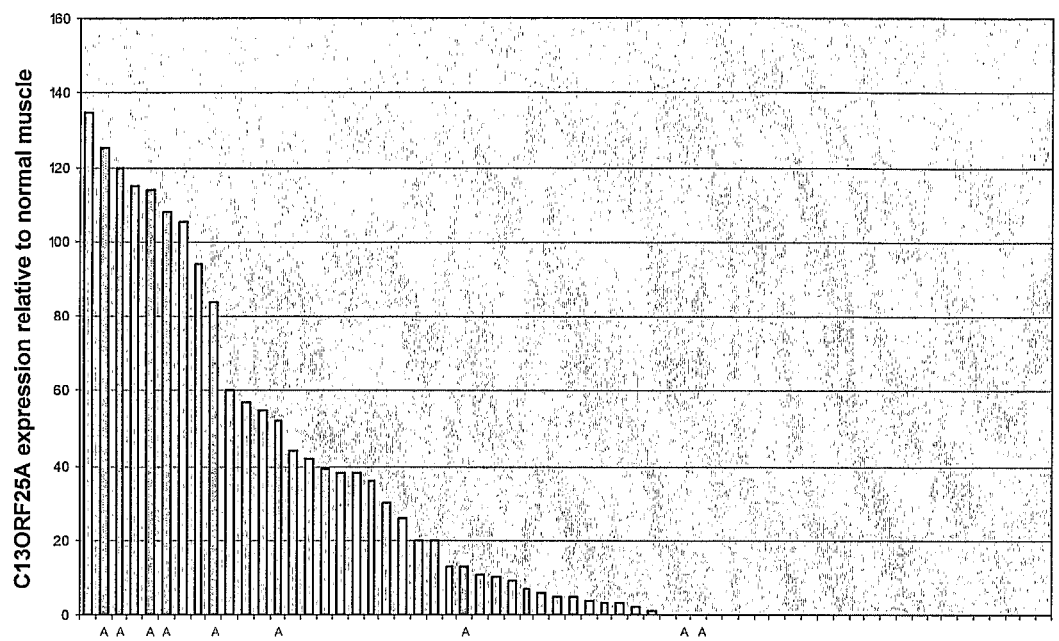

Expression of C13ORF25 was also determined in the same set of rhabdomyosarcoma cDNA samples. Results are shown in FIG. 2B. Whilst a majority of samples with genomic amplification also show relatively high expression of C13ORF25, crucially there are 2 samples which show genomic gain but no expression. This is not the case with GPC5. Furthermore, roughly half of the samples do not show detectable expression of C13ORF25, in contrast to GPC5 where many of the samples show expression levels much higher than that seen in muscle. Whilst these data suggest that expression of C13ORF25A is affected by genomic gain, its impact on rhabdomyosarcomagenesis (if any) is likely to be less significant than that of GPC5.

Clinico-Pathological Correlations

Genomic gain of GPC5 copies appears to occur primarily in younger children. Of the 83 samples with associated age data is aged <21, all 13 amplified samples were aged between 0-10 years old whereas 42 of the non-amplified samples were aged 0-10 years and the remaining 28 were aged 10-21. There is significant heterogeneity in the age at diagnosis of patients with gain of genomic copies of GPC5 and those without gain of genomic copies of tumours: Likelihood Ratio=8.332 n=83 p=0.0038. There is no significant difference observed between GPC5 expression or GPC5 amplification and grade, stage, time to death or event free survival.

GPC5 Downregulation and Cell Proliferation.

Figure 3:
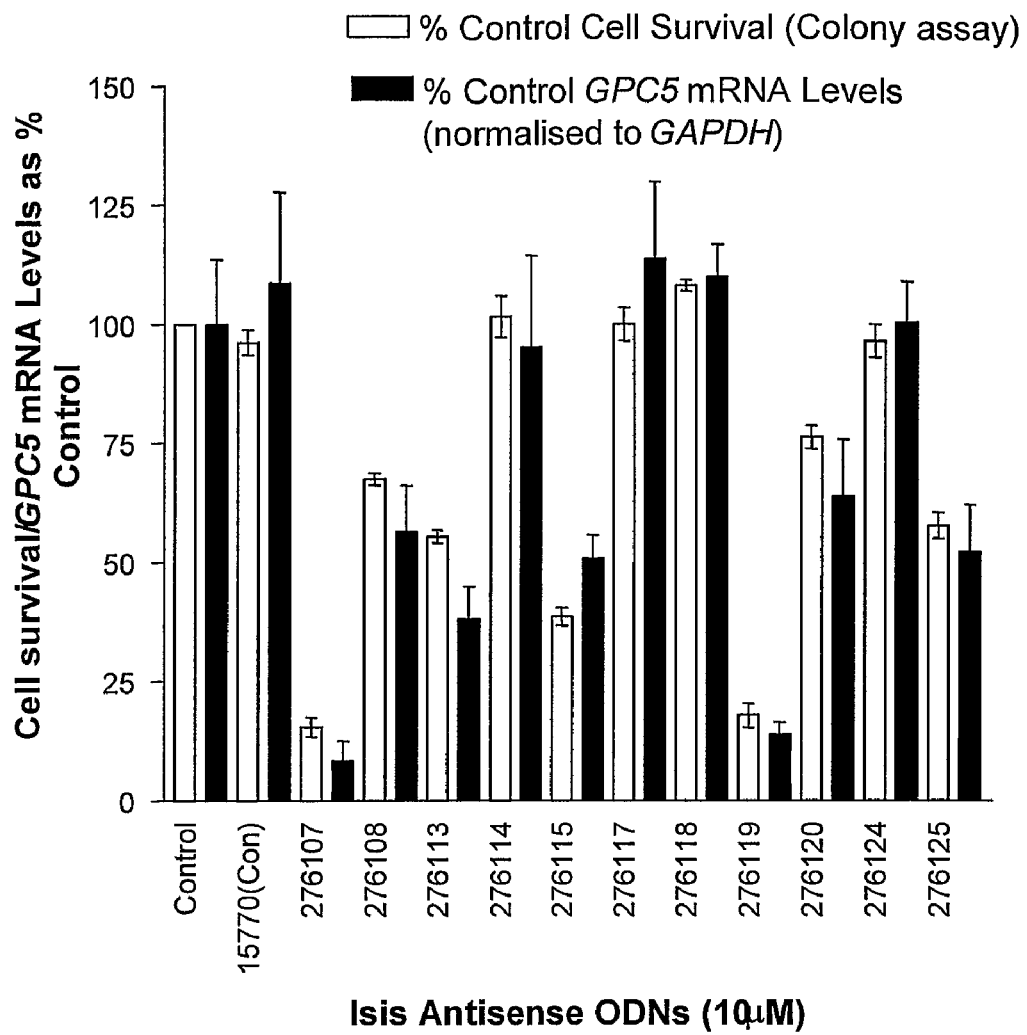
FIG. 3 shows the effect of GPC5 antisense oligonucleotides on GPC5 mRNA levels and cell survival in K562 cells. Panel A shows data for 13 representative GPC5-targeted oligonucleotides relative to the control oligonucleotide 15770. Panels B and C show dose-response curves for one active oligonucleotide (276107) relative to a different control oligonucleoide, designated 276124.

Twenty GPC5 targeted antisense oligonucleotides were screened for the ability to significantly reduce both GPC5 levels and cell survival. Two active compounds, ISIS 276107 and ISIS 276119, were identified in this primary screen, reducing GPC5 levels to less than 30% control levels and reducing cell survival by greater than 80% (FIG. 3A). These results are compared to two other typical ASOs from this screen where both GPC5 levels and cell survival were unaffected. Although preliminary, these data suggest a correlation between downregulation of GPC5 expression and loss of cell viability. FIGS. 3B and C show the effects of ISIS 276107 and a control compound (ISIS 276124) at varying concentrations in the same assay. Panel B shows the percentage of colonies in a soft agar clonogenic assay compared to sham-treated levels following treatment with the active compound ISIS 107 and a control compound ISIS 276124, which has been found not to affect cell viability or GPC5 expression (data not shown). HL-60, a control leukaemic cell line which does not express GPC5, shows no decrease in colony number following treatment with either the active ISIS 107 or the control ISIS 124 compound. Panel C shows the percentage expression of GPC5 relative to sham-treated levels 24 hours after treatment.

GPC5 Expression in Prostate and Breast Cancer

For prostate samples, the assay was carried out as for the rhabdomyosarcoma samples described above, except that expression was measured relative to normal prostate cDNA synthesized from a commercially available normal prostate RNA pool as opposed to normal muscle cDNA.

Figure 4:
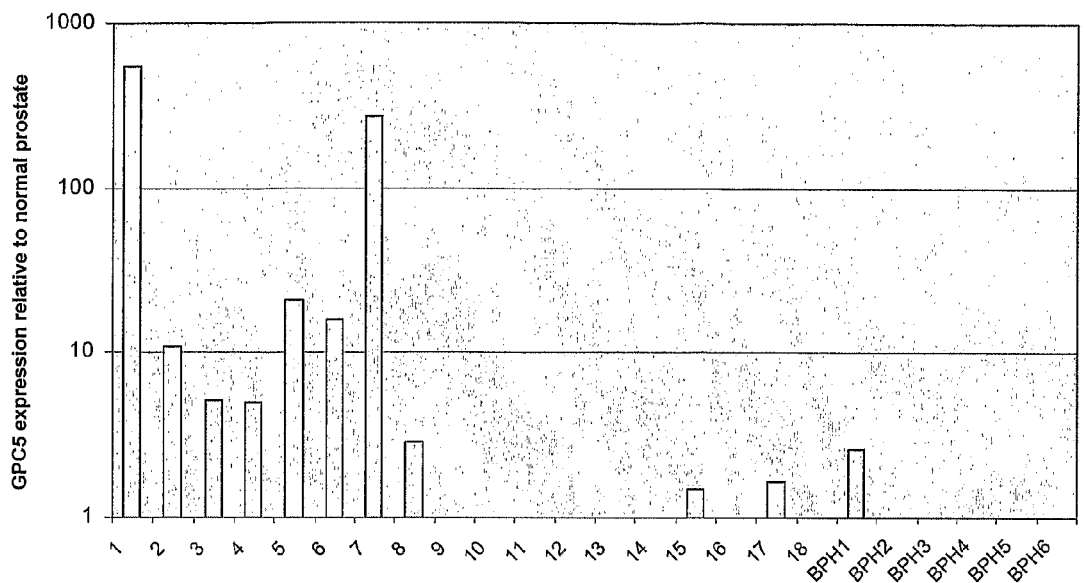
FIG. 4A shows the level of GPC5 mRNA expression in 18 prostate cancer samples and 6 benign prostate hyperplasia samples, as compared to normal prostate.
FIG. 4B shows the overall difference in GPC5 expression between prostate cancer and benign prostatic hyperplasia.
Figure 4:
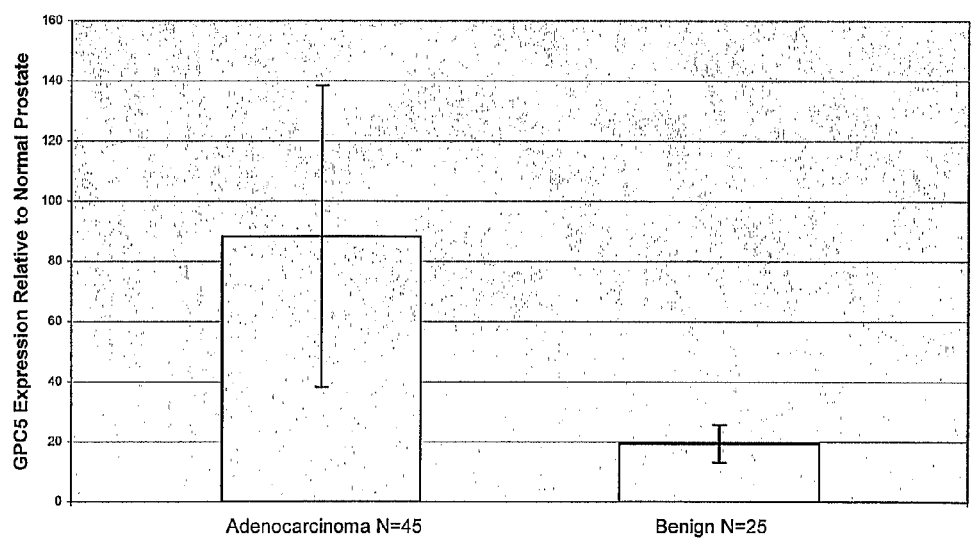

FIG. 4A shows the level of expression of GPC5 in a number of individual samples. Several samples show greater expression than normal prostate. Furthermore, there is a significantly greater expression in prostate cancer compared with Benign Prostatic Hyperplasia (BPH) Mann-Whitney U=16 p=0.011 N=24. However the significance of results should be interpreted with caution as there are only six BPH samples. Taken together this data does suggest a potential role for GPC5 overexpression in the development of prostate cancer.

FIG. 4B shows overall GPC5 expression in a larger sample of prostate adenocarcinoma (n=45) and benign prostate hyperplasia (n=25) relative to normal prostate tissue. The samples used here include those for which results are shown in FIG. 4A. For the breast cancer samples shown in FIG. 5A, measurement was performed relative to normal breast cDNA biopsy tissue as opposed to normal muscle cDNA, and was performed in duplicate instead of triplicate.

The data shows relative overexpression of GPC5 in some samples. The highest value was in biopsies taken from lymph nodes with metastasis. This suggests potential involvement of GPC5 in tumourigenesis in these samples.

Figure 5:
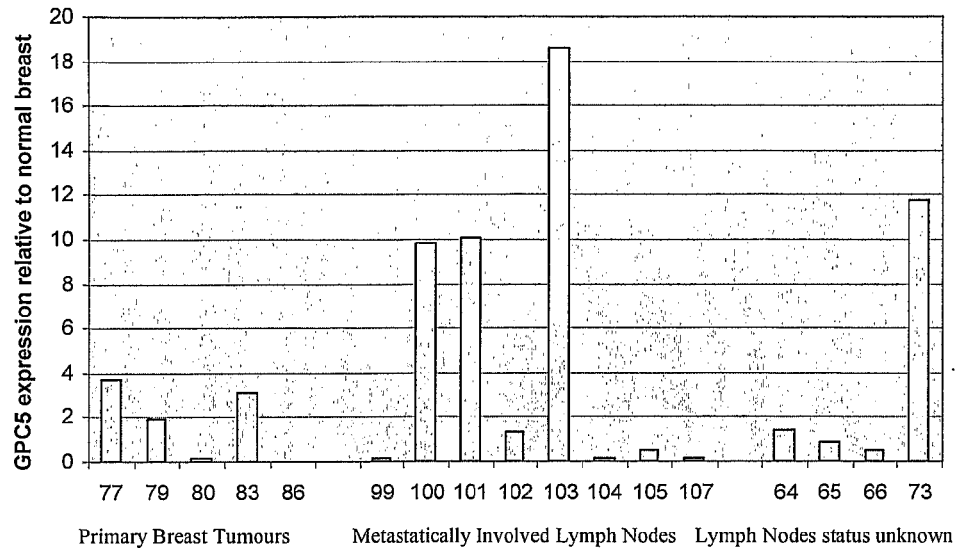
FIG. 5A shows GPC5 mRNA expression in breast cancer samples relative to normal breast biopsy tissue.
FIG. 5B shows the number of tumours of stage 1, 2 or 3 which overexpress GPC5 relative to normal breast tissue in a sample of 44 breast tumours.
Figure 5:
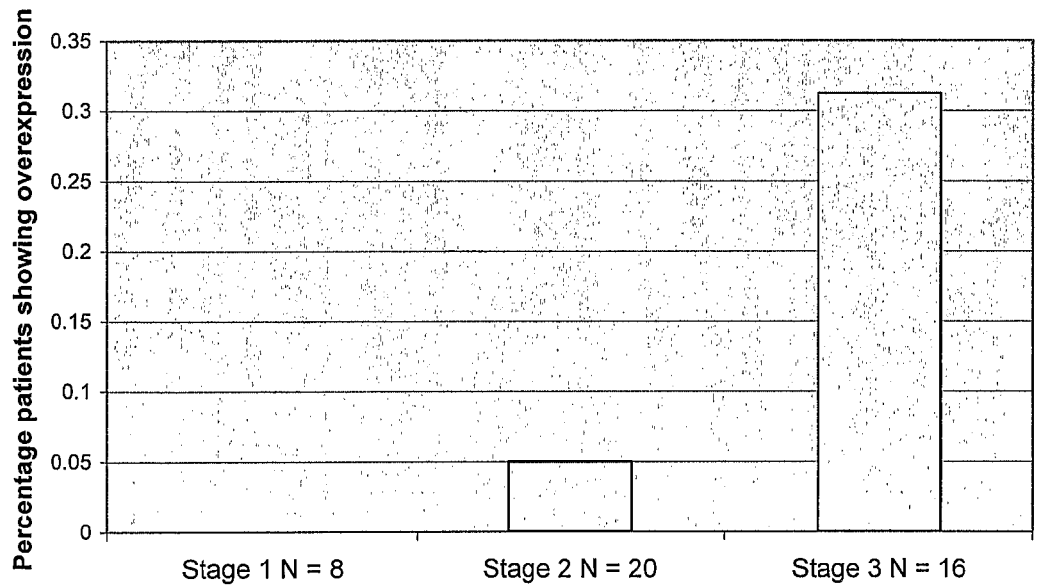

Expression of GPC5 was then measured by TaqMan analysis in seven normal breast samples and 44 breast cancer samples. The mean normal breast GPC5 expression and 95% confidence intervals were calculated. Any tumour sample in which GPC5 expression exceeded the upper confidence interval for normal samples was said to overexpress GPC5. The samples were grouped according to the stage of the disease (stage 1, 2 or 3). 5 out of the 6 samples which show overexpression are stage 3. There is a significant difference in the stage of those samples which overexpress GPC5; Fisher's Exact Test p=0.017 n=44 (FIG. 5B).

Correlation with MYCN Expression

For some of the samples we already had information about expression of MYCN from a previous TaqMan study (data not shown). It was found that in ERMS and ARMS with a confirmed PAX/FOXO1A translocation that expression of GPC5 correlated significantly with expression of MYCN: Spearman's Rho=0.497 n=38 p=0.002 and Spearman's Rho=0.399 n=26 p=0.043 respectively.

Regulation of GPC5 expression by the Wilms' Tumour gene (WT1) product.

Figure 6A:
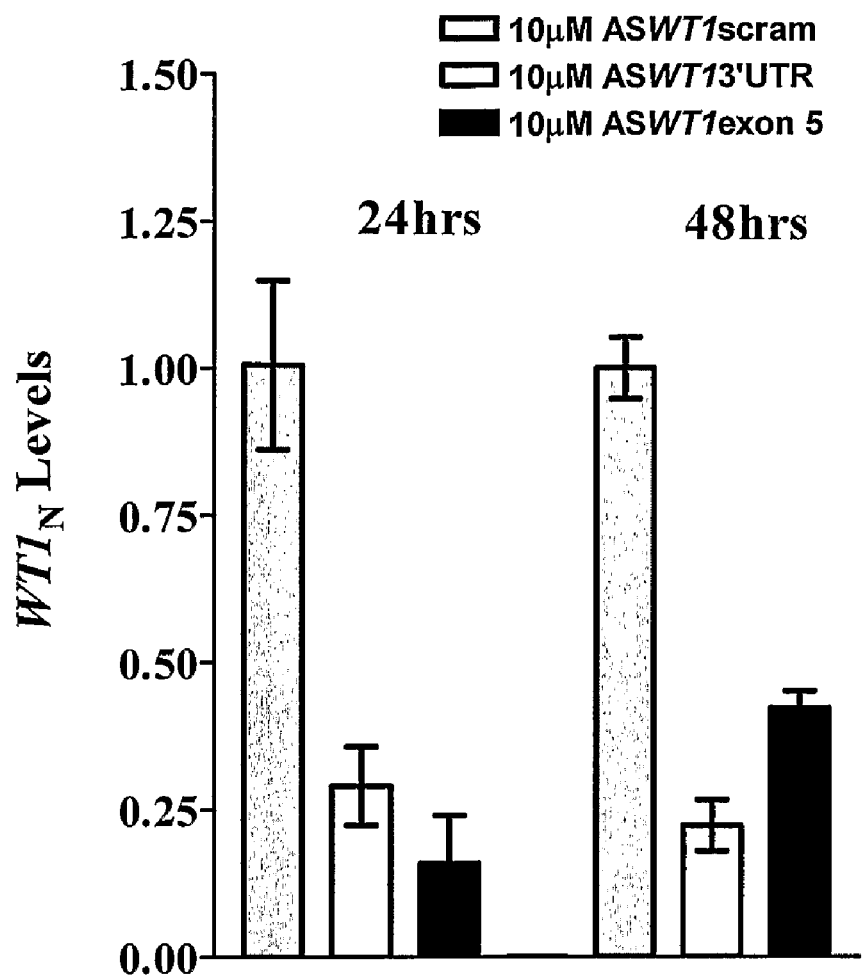
FIG. 6 shows the effect of WT1 antisense oligonucleotides on WT1 and GPC5 mRNA levels in K562 cells, both 24 and 48 hours after treatment, suggesting that WT1 may regulate GPC5 expression.
Figure 6B:
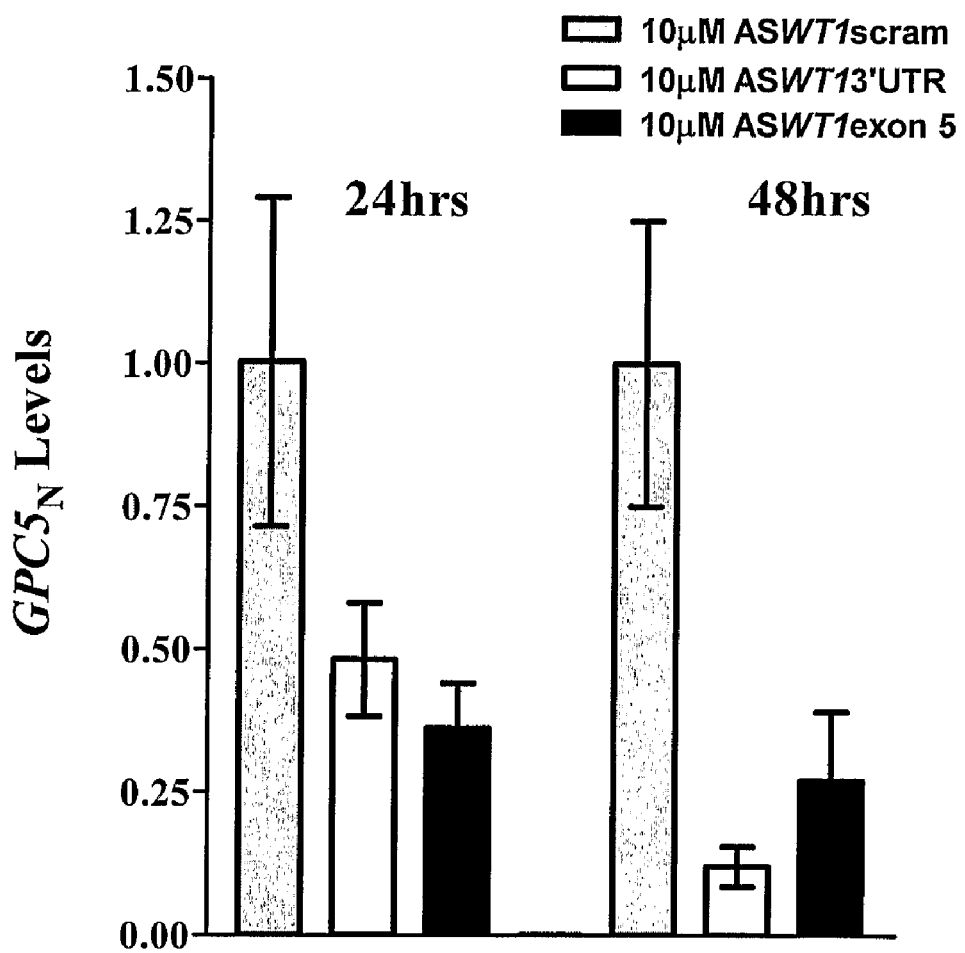
Figure 7:
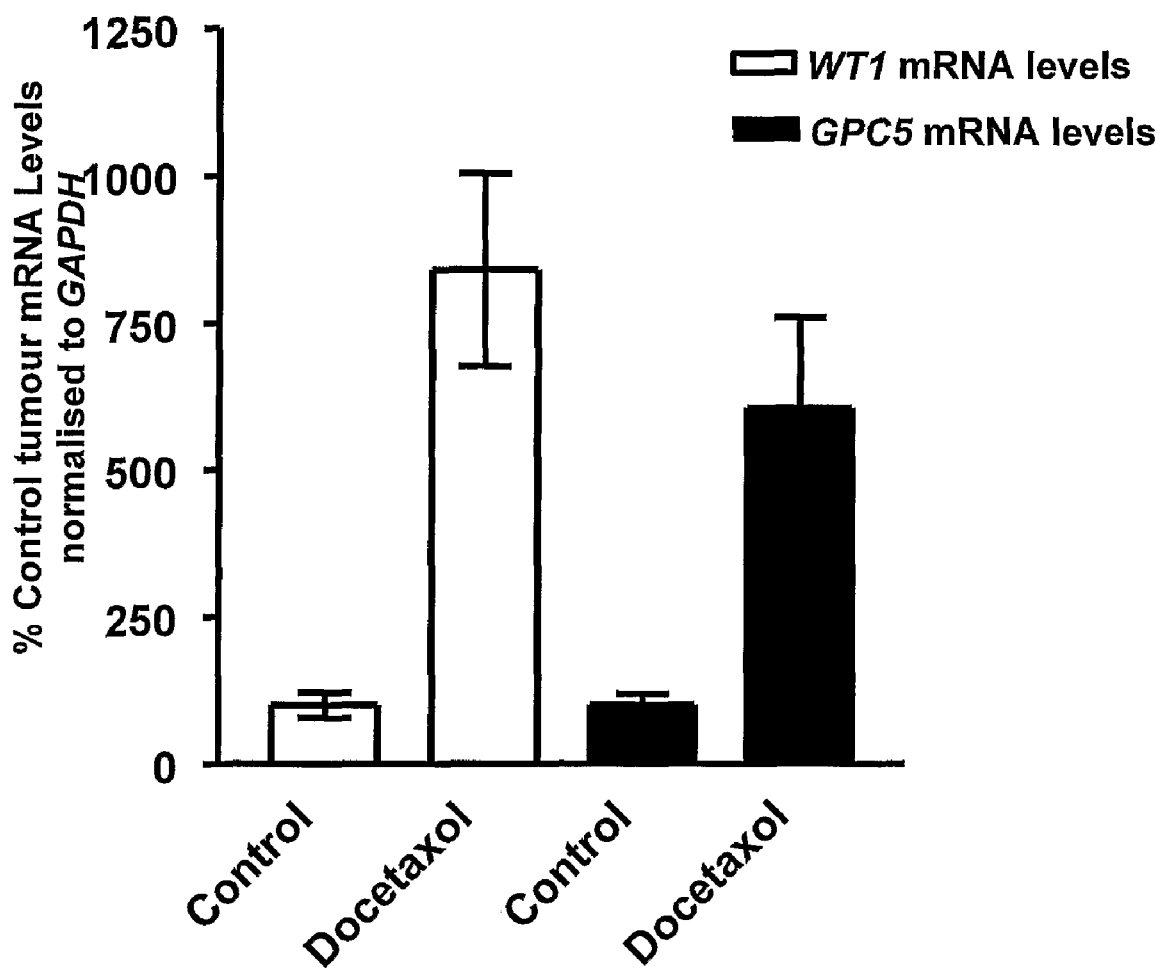
FIG. 7 shows upregulation of both WT1 and GPC5 mRNA in PC3M tumors treated with docetaxol.

Previous gene profiling studies following treatment of K562 cells with WT1 directed ASOs, identified GPC5 as a putative WT1 target gene (manuscript in preparation). Downregulation of GPC5 expression following WT1 antisense treatment and correlating with reduced WT1 expression was confirmed in independent experiments (see FIG. 6). Similarly, preliminary in vivo studies have demonstrated downregulation of GPC5 in PC3M prostate cancer cells grown as subcutaneous implants in athymic nude mice treated with WT1 antisense: A 50% decrease in WT1 expression levels in ASWT1exon5 mice was reflected by a 30% reduction in GPC5 expression (data not shown). Direct transcriptional regulation of GPC5 by WT1 is likely since GPC5 has two WT1 consensus binding sites in its promoter region.

Using the same in vivo model system we have obtained preliminary evidence of upregulation of both WT1 and GPC5 expression in PC3M tumours following treatment of the mice with docetaxol (15 mg/kg): A nine fold increase in WT1 expression was reflected by a 5 fold increase in GPC5 expression. These studies raise the possibility that GPC5 overexpression may be induced by cancer chemotherapy. The PC3M tumour model is relatively resistant to cytotoxic drug treatment giving rise to the speculation that upregulation of GPC5 expression may contribute to poor response to therapy.

GPC5 Overexpression and Cell Proliferation

In order to test if overexpression of GPC5 could confer oncogenic properties, a GPC5 construct was made under the control of a CMV (Cyto-Megalo Virus) promoter in order to constitutively express GPC5. This construct was tested by in vitro translation and was shown to produce the appropriate size protein (63 K Daltons) (see FIG. 8C). RMS cell line T91-95 was stably transfected and healthy colonies were picked. T91-95 is an RMS cell line which expresses both GPC5 and MYCN at levels similar to that of normal muscle. 5 GPC5 transfected and 5 empty vector control transfected colonies were randomly selected and subjected to a cell proliferation assay.

Cells were plated at 7500 cells per 24 well plate in triplicate repeats. In order to allow cells to recover and to normalize for potential variations in plating efficiency and cell counting errors the first measurement was taken at 16 hrs. The proliferation assay uses a calorimetric PNNAG assay in which absorbance is proportional to number of cells. Log Normalized Growth is calculated as the mean natural logarithm of absorbance of triplicates at 64 hours minus the mean natural logarithm of absorbance of triplicates at 16 hours. There is a significant difference between the Log Normalized Growth in GPC5 overexpressing colonies compared to control colonies p=0.027 t=2.70 n=10 (FIG. 8A).

Figure 8:
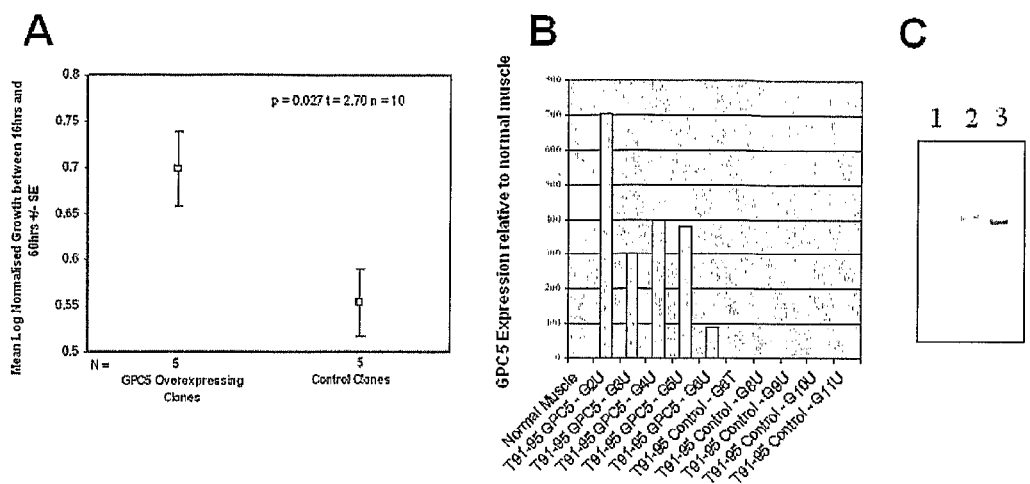
FIG. 8 shows the effect of GPC5 overexpression in the RMS cell line T91-95. A: Difference in proliferation between 5 GPC5 overexpressing colonies and 5 mock-transfected control colonies. B: Difference in expression of GPC5 as measured by TaqMan assay between GPC5 overexpressing colonies and control colonies. C: Western Blot of an In Vitro Translation; Lane 1 water (negative control), Lane 2 pCMV-TNT-GPC5 (63 Kda), Lane 3 Luciferase (61 Kda positive control). Protein was translated so as to incorporate biotin labelled lysine residues. Colour was developed using streptavidin-alkaline phosphatase and appropriate colorimetric reagents.

FIG. 8B shows the expression level of GPC5 as measured by TaqMan assay in GPC5 overexpressing colonies and control colonies, as compared to normal muscle tissue.

Discussion

Our data support and characterize a potential role for the GPC5 gene, a cell surface heparan sulfate proteoglycan, in the development of RMS. Analysis of previous data indicated differential overexpression corresponding to the 13q31-32 region, which harbors the GPC5 gene, was found in cases which amplify the region and also in some cases without amplification of both the alveolar and embryonal subtypes. This data was mirrored by the quantitative analysis of GPC5 copy number and expression and together suggests that overexpression of GPC5 is important in the pathogenesis of RMS of both subtypes. The data is also consistent with gene expression being up-regulated by mechanisms other than genomic amplification.

The Glypicans are a family of conserved cell surface heparan sulfate proteoglycans which are believed to modulate the activity of heparan binding growth factors such as FGFs (fibroblast growth factors) and Wnts (25). Deregulation of other members of the glypican family has been implicated in development of a number of tumors. GPC1 (Glypican-1) has been shown to be overexpressed in human pancreatic cancer and to positively regulate the action of HB-EGF (Heparan Binding Epidermal Growth Factor) and FGF2 (Fibroblast Growth Factor 2) (26). Furthermore, stable transfection of a GPC1 antisense construct in the GPC1 overexpressing pancreatic cancer cell line PANC-1 decreased tumourgenicity (27). GPC1 is similarly overexpressed in breast cancer and modulates the activity of a number of heparan binding growth factors (28). GPC3 has been shown to aberrantly overexpress in 7/10 neuroblastoma cell lines, 4/4 primary neuroblastoma samples and 7/7 primary Wilms tumour samples (29). Expression in these tumours is shown to correlate with IGF2 expression (Insulin-like Growth Factor II) a gene which is frequently overexpressed in RMS (30).

Examination of the only two annotated genes in the 13q31 region has demonstrated that the 13q31 amplification in RMS includes the gene GPC5 but not GPC6. Although no other sequences from the region have been shown to be expressed, it remains possible that as yet uncharacterized genes exert an effect. In contrast to Yu et al our amplification appears to peak centrally at the gene GPC5. As we have demonstrated a functional consequence of elevated protein levels of GPC5 in RMS cells it is likely that the overexpression of this gene associated with amplification in lymphoma cell lines is exerting a similar effect. In addition, we note amplification and/or overexpression from 13q31-32 in another type of soft tissue sarcoma, namely leiomyosarcomas which resemble smooth muscle tissue (11, 20) (Unpublished Data). Other sarcoma types have also been documented with amplification of this region and therefore it is possible that up regulation of this gene is a more general feature of soft tissue sarcomas. This may extend to other tumour types described with amplification of this region such as breast cancer, small-cell lung cancer, medulloblastoma and glioblastoma (11-17). Preliminary data for the expression levels of GPC5 in prostate and breast cancers relative to corresponding normal tissues suggests that some of these tumours aberrantly overexpress this gene.

Whilst amplification and/or overexpression of GPC5 are a frequent occurrence in RMS, we provide no evidence that these are likely to be of use as clinical markers of prognosis. In the series studied there does not appear to be a significant difference in the survival characteristics of patients with tumors amplifying or overexpressing GPC5 compared to those that do not. Furthermore, amplification seems to predominate in patients between 0-10 years; a clinical group with generally improved prognosis (31). Further analysis of a larger cohort of samples, perhaps using a tissue array, may identify sub-groups of rhabdomyosarcoma in which deregulation of GPC5 is clinically significant. Another possibility is that detection of GPC5 protein in blood serum of patients may serve as a marker of RMS or other cancers in a similar manner to which GPC1 protein in the serum identifies patients with hepatocellular carcinoma (32).

The fact that expression of GPC5 correlates with expression of the oncogene MYCN is further evidence to support the role of GPC5 in the tumourigenesis of RMS. It is unclear from this study whether the relationship is causal. Certainly GPC5 overexpression in our in vitro model does not cause overexpression of MYCN. It is noteworthy, however, that the sequence proximally upstream of the start of GPC5 transcription contains an E-box (MYC trans-activation site) consensus sequence suggesting potential direct trans-activation of GPC5 by MYCN.

Potentially as significant, is the apparent regulation of GPC5 by the WT1 gene product. Although not proven to be oncogenic, WT1 may contribute to the maintenance of a malignant phenotype in leukaemias and the large range of solid tumours where its expression is deregulated. In addition, WT1 has been implicated in drug resistance mechanisms and is being investigated as a potential target for cancer therapy. Our studies so far indicate that GPC5 may well mediate at least some of the downstream biological effects of WT1 expression making GPC5, potentially, the more effective target for therapeutic intervention.

In conclusion, we have established that GPC5 is amplified and/or overexpressed in RMS and that GPC5 is a novel oncogene. GPC5 is particularly attractive target for novel therapies for a number of reasons. First, because it is a cell surface protein it is physically accessible to a number of potential anti-GPC5 therapies. Second, because it potentially acts as a modulator of multiple growth factors therapies which reduce the function of GPC5 could therefore affect multiple tumorigenic pathways. Third, because it is likely to be important in the tumorigenesis of a number of other cancer types.

REFERENCES

1. Galili, N., Davis, R. J., Fredericks, W. J., Mukhopadhyay, S., Rauscher, F. J., 3rd, Emanuel, B. S., Rovera, G., and Barr, F. G. Fusion of a fork head domain gene to PAX3 in the solid tumour alveolar rhabdomyosarcoma. Nat Genet, 5: 230-235, 1993.
2. Shapiro, D. N., Sublett, J. E., Li, B., Downing, J. R., and Naeve, C. W. Fusion of PAX3 to a member of the forkhead family of transcription factors in human alveolar rhabdomyosarcoma. Cancer Res, 53: 5108-5112, 1993.
3. Davis, R. J., D'Cruz, C. M., Lovell, M. A., Biegel, J. A., and Barr, F. G. Fusion of PAX7 to FKHR by the variant t(1;13)(p36;q14) translocation in alveolar rhabdomyosarcoma. Cancer Res, 54: 2869-2872, 1994.
4. Gordon, A. T., Brinkschmidt, C., Anderson, J., Coleman, N., Dockhorn-Dworniczak, B., Pritchard-Jones, K., and Shipley, J. A novel and consistent amplicon at 13q31 associated with alveolar rhabdomyosarcoma. Genes Chromosomes.Cancer, 28: 220-226, 2000.
5. Bridge, J. A., Liu, J., Qualman, S. J., Suijkerbuijk, R., Wenger, G., Zhang, J., Wan, X., Baker, K. S., Sorensen, P., and Barr, F. G. Genomic gains and losses are similar in genetic and histologic subsets of rhabdomyosarcoma, whereas amplification predominates in embryonal with anaplasia and alveolar subtypes. Genes Chromosomes Cancer, 33: 310-321, 2002.
6. Menghi-Sartorio, S., Mandahl, N., Mertens, F., Picci, P., and Knuutila, S. DNA copy number amplifications in sarcomas with homogeneously staining regions and double minutes. Cytometry, 46: 79-84, 2001.
7. Pandita, A., Zielenska, M., Thorner, P., Bayani, J., Godbout, R., Greenberg, M., and Squire, J. A. Application of comparative genomic hybridization, spectral karyotyping, and microarray analysis in the identification of subtype-specific patterns of genomic changes in rhabdomyosarcoma. Neoplasia, 1: 262-275, 1999.
8. Bridge, J. A., Liu, J., Weibolt, V., Baker, K. S., Perry, D., Kruger, R., Qualman, S., Barr, F., Sorensen, P., Triche, T., and Suijkerbuijk, R. Novel genomic imbalances in embryonal rhabdomyosarcoma revealed by comparative genomic hybridization and fluorescence in situ hybridization: an intergroup rhabdomyosarcoma study. Genes Chromosomes.Cancer, 27: 337-344, 2000.
9. Weber-Hall, S., Anderson, J., McManus, A., Abe, S., Nojima, T., Pinkerton, R., Pritchard-Jones, K., and Shipley, J. Gains, losses, and amplification of genomic material in rhabdomyosarcoma analyzed by comparative genomic hybridization. Cancer Res, 56: 3220-3224, 1996.
10. Roberts, I., Gordon, A., Wang, R., Pritchard-Jones, K., Shipley, J., and Coleman, N. Molecular cytogenetic analysis consistently identifies translocations involving chromosomes 1, 2 and 15 in five embryonal rhabdomyosarcoma cell lines and a PAX-FOXO1A fusion gene negative alveolar rhabdomyosarcoma cell line. Cytogenet Cell Genet, 95: 134-142, 2001.
11. Wang, R., Titley, J. C., Lu, Y. J., Summersgill, B. M., Bridge, J. A., Fisher, C., and Shipley, J. Loss of 13q14-q21 and gain of 5p14-pter in the progression of leiomyosarcoma. Mod Pathol, 16: 778-785, 2003.
12. Larramendy, M. L., Tarkkanen, M., Blomqvist, C., Virolainen, M., Wiklund, T., Asko-Seljavaara, S., Elomaa, I., and Knuutila, S. Comparative genomic hybridization of malignant fibrous histiocytoma reveals a novel prognostic marker. Am J Pathol, 151: 1153-1161, 1997.
13. Yu, W., Inoue, J., Imoto, I., Matsuo, Y., Karpas, A., and Inazawa, J. GPC5 is a possible target for the 13q31-q32 amplification detected in lymphoma cell lines. J Hum Genet, 48: 331-335, 2003.
14. Ojopi, E. P., Rogatto, S. R., Caldeira, J. R., Barbieri-Neto, J., and Squire, J. A. Comparative genomic hybridization detects novel amplifications in fibroadenomas of the breast. Genes Chromosomes Cancer, 30: 25-31, 2001.
15. Schmidt, H., Wurl, P., Taubert, H., Meye, A., Bache, M., Holzhausen, H. J., and Hinze, R. Genomic imbalances of 7p and 17q in malignant peripheral nerve sheath tumors are clinically relevant. Genes Chromosomes Cancer, 25: 205-211, 1999.
16. Weber, R. G., Sabel, M., Reifenberger, J., Sommer, C., Oberstrass, J., Reifenberger, G., Kiessling, M., and Cremer, T. Characterization of genomic alterations associated with glioma progression by comparative genomic hybridization. Oncogene, 13: 983-994, 1996.
17. Reardon, D. A., Jenkins, J. J., Sublett, J. E., Burger, P. C., and Kun, L. K. Multiple genomic alterations including N-myc amplification in a primary large cell medulloblastoma. Pediatr Neurosurg, 32: 187-191, 2000.
18. Naumann, S., Reutzel, D., Speicher, M., and Decker, H. J. Complete karyotype characterization of the K562 cell line by combined application of G-banding, multiplex-fluorescence in situ hybridization, fluorescence in situ hybridization, and comparative genomic hybridization. Leuk Res, 25: 313-322, 2001.
19. Lu, Y. J., Williamson, D., Clark, J., Wang, R., Tiffin, N., Skelton, L., Gordon, T., Williams, R., Allan, B., Jackman, A., Cooper, C., Pritchard-Jones, K., and Shipley, J. Comparative expressed sequence hybridization to chromosomes for tumor classification and identification of genomic regions of differential gene expression. Proc Natl Acad Sci U S A, 98: 9197-9202, 2001.
20. Lu, Y. J., Williamson, D., Wang, R., Summersgill, B., Rodriguez, S., Rogers, S., Pritchard-Jones, K., Campbell, C., and Shipley, J. Expression profiling targeting chromosomes for tumor classification and prediction of clinical behavior. Genes Chromosomes Cancer, 38: 207-214, 2003.
21. Smedley, D., Hamoudi, R., Clark, J., Warren, W., Abdul-Rauf, M., Somers, G., Venter, D., Fagan, K., Cooper, C., and Shipley, J. The t(8;13)(p11;q11-12) rearrangement associated with an atypical myeloproliferative disorder fuses the fibroblast growth factor receptor 1 gene to a novel gene RAMP. Hum Mol Genet, 7: 637-642, 1998.
22. Perani, M., Ingram, C. J., Cooper, C. S., Garrett, M. D., and Goodwin, G. H. Conserved SNH domain of the proto-oncoprotein SYT interacts with components of the human chromatin remodelling complexes, while the QPGY repeat domain forms homo-oligomers. Oncogene, 22: 8156-8167, 2003.
23. Landegren, U. Measurement of cell numbers by means of the endogenous enzyme hexosaminidase. Applications to detection of lymphokines and cell surface antigens. J Immunol Methods, 67: 379-388, 1984.
24. Veugelers, M., De Cat, B., Delande, N., Esselens, C., Bonk, I., Vermeesch, J., Marynen, P., Fryns, J. P., and David, G. A 4-Mb BAC/PAC contig and complete genomic structure of the GPC5/GPC6 gene cluster on chromosome 13q32. Matrix Biol, 20: 375-385, 2001.
25. Filmus, J. Glypicans in growth control and cancer. Glycobiology, 11: 19R-23R, 2001.
26. Kleeff, J., Ishiwata, T., Kumbasar, A., Friess, H., Buchler, M. W., Lander, A. D., and Korc, M. The cell-surface heparan sulfate proteoglycan glypican-1 regulates growth factor action in pancreatic carcinoma cells and is overexpressed in human pancreatic cancer. J Clin Invest, 102: 1662-1673, 1998.
27. Kleeff, J., Wildi, S., Kumbasar, A., Friess, H., Lander, A. D., and Korc, M. Stable transfection of a glypican-1 antisense construct decreases tumorigenicity in PANC-1 pancreatic carcinoma cells. Pancreas, 19: 281-288, 1999.
28. Matsuda, K., Maruyama, H., Guo, F., Kleeff, J., Itakura, J., Matsumoto, Y., Lander, A. D., and Korc, M. Glypican-1 is overexpressed in human breast cancer and modulates the mitogenic effects of multiple heparin-binding growth factors in breast cancer cells. Cancer Res, 61: 5562-5569, 2001.
29. Saikali, Z. and Sinnett, D. Expression of glypican 3 (GPC3) in embryonal tumors. Int J Cancer, 89: 418-422, 2000.
30. Khan, J., Wei, J. S., Ringner, M., Saal, L. H., Ladanyi, M., Westermann, F., Berthold, F., Schwab, M., Antonescu, C. R., Peterson, C., and Meltzer, P. S. Classification and diagnostic prediction of cancers using gene expression profiling and artificial neural networks. Nat Med, 7: 673-679, 2001.

31. Crist, W. M., Anderson, J. R., Meza, J. L., Fryer, C., Raney, R. B., Ruymann, F. B., Breneman, J., Qualman, S. J., Wiener, E., Wharam, M., Lobe, T., Webber, B., Maurer, H. M., and Donaldson, S. S. Intergroup rhabdomyosarcoma study-IV: results for patients with nonmetastatic disease. J Clin.Oncol., 19: 3091-3102, 2001.

32. Capurro, M., Wanless, I. R., Sherman, M., Deboer, G., Shi, W., Miyoshi, E., and Filmus, J. Glypican-3: a novel serum and histochemical marker for hepatocellular carcinoma. Gastroenterology, 125: 89-97, 2003.

33. Ota, A. et al. Identification and Characterization of a Novel Gene, C13orf25, as a Target for 13q31-q32 Amplification in Malignant Lymphoma. Cancer Res., 64: 3087-3095, 2004.

The disclosure of all references cited herein, insofar as it may be used by those skilled in the art to carry out the invention, is hereby specifically incorporated herein by cross-reference.

The invention claimed is:

1. A method of inhibiting proliferation of a target cell, comprising contacting the cell with a GPC5 antagonist selected from the group consisting of antisense RNA, antisense DNA and dsRNA, which comprises a nucleic acid sequence complementary to the sequence of GPC5 mRNA or pre-mRNA.

2. A method according to claim 1 wherein the target cell inappropriately expresses or overexpresses GPC5.

3. A method according to claim 1 wherein the cell inappropriately expresses or overexpresses WT1.

4. A method according to claim 1 wherein the cell is a cancer cell.

5. A method according to claim 4 wherein the cancer is rhabdomyosarcoma, lymphoma, non-small cell lung cancer, bladder cancer, breast cancer, prostate cancer, a neuroglial tumour, squamous cell carcinoma of the head and neck, leukemia, leiomyosarcoma, liposarcoma, malignant fibrous histocytoma of bone or soft tissues, melanoma, mesothelioma, thyroid cancer, lung cancer, testicular cancer or ovarian cancer.

6. A method according to any one of claims 1 to 5 wherein the cell does not carry a chromosomal amplicon at 13q31.

7. A method according to claim 1 wherein the GPC5 antagonist inhibits expression of functional GPC5 at the cell surface.

8. A method according to claim 1 wherein the GPC5 antagonist is selected from the group consisting of antisense RNA, RNAi and siRNA.

9. A method according to any one of claim 1 further comprising contacting the cell with a therapeutic agent.

10. A method according to claim 9 wherein the GPC5 antagonist increases the sensitivity of the cell to the therapeutic agent.

* * * * *